OTHER PUBLICATIONS

United States Patent [19]
Chong et al.
[11] Patent Number: 6,037,448
[45] Date of Patent: Mar. 14, 2000
[54] SYNTHETIC PEPTIDES FOR A RUBELLA VACCINE
[75] Inventors: Pele Chong, Richmond Hill; **Shirley Gillam

Hopp, T.P. and K.R. Woods. 1981. Prediction of protein antigenic determinants from amino acid sequence. Proc. Natl. Acad. Sci. USA 78:3824–3828.

Ho–Terry, L, A. Cohen, and P. Londesborough. 1982. Rubella virus wild–type and RA27/3 strains: a comparison by polyacrylamide–gel electrophoresis and radioimmune precipitation. J. Med. Microbiol. 15:393–398.

Ilonen, J. and A. Salmi. 1986. Comparison of HLA–DW1 and DW2 positive adherent cell in antigen presentation to heterozygous T cell lines: A low rubella antigen–specific response associated with HLA–DW2. 1986. Human Immunology. 17:94–101.

Ishii,K., N. Nakazono, H. Sawada, K. Fukuda, A. Wakisaka, J. Moriuchi, Y. Nakai, T. Kano and M. Alzawa. 1981. Host factor and susceptibility to rubella virus infection: The association of HLA antigens. J. Med. Virol. 7:287–297.

Kato, S., S. Muranaka, I. Takakura, M. Kimura and K. Tsun. 1982. HLA–DR antigen and the rubella–specific immune response in man. Tissue Antigen. 19:140–145.

Lerner, R. A., N. Green, H. Alexander, F.–T. Liu, J. G. Sutcliffe and T. M. Shinnick, 1981. Chemically synthesized peptides predicted from the nucleotide sequence of the hepatitis B virus genome elicit antibodies reactive with the native envelope protein of Dane particles. Proc. Natl. Acad. Sci. USA 78:3403–3407.

Liebhaber, H. 1970. Measurement of rubella antibody by haemagglutination. I. Variables affecting rubella haemagglutination. J. Immunol. 104:818–825.

Loo, T.W., I. MacMonald, D.M. Clark, M. Trudel, A. Tingle and S. Gillam. 1986. Detection of antibodies to individual proteins of rubella virus. J. Virol. Meth. 13:149–159.

Martin, R., P. Marquardt, S. O'Shea, M. Borkenstein and H. W. Kreth. 1989. Virus–specific and autoreactive T cell lines isolated from cerebrospinal fluid of a patient with chronic rubella panencephalitis. J. of Neuroimmunol. 23:1–10.

Matthews, R. E. F. 1982. Classification and nomenclature of viruses. Intervirology 17:1–199.

Mazancourt, A. de, M. N. Waham, J. C. Nicolasand, J. S. Wolinsky. 1986. Antibody response to the rubella virus structural proteins in infants with the cogenital rubella syndrome. J. Med. Virol. 19:111–122.

Milich, D. R., D. L. Peterson, G. G. Leroux–Roels., R. A. Lerner and F. V. Chisari. 1985. Genetic regulation of the immune response to hepatitis B surface antigen (HBsAg): VI. T cell fine specificity. J. Immunol. 134:4203–4211.

Milich, D. R., A. McLachlan, G. B. Thornton and J. L. Hughes. 1987. Antibody production to the nucleocapsid and envelope of the hepatitis B virus primed by a single synthetic T cell site. Nature 329:547–549.

Milich, D. R., J. L. Hughes, A. McLachlan, G. B. Thornton and A. Moriarty. 1988. Hepatitis B synthetic Immunogen comprised of nucleocapsid T–cell sites and an envelope B–cell epitope. Proc. Natl. Acad. Sci. USA 85:1610–1614.

Milich, D. R., 1988. Synthetic T and B cell recognition sites: Implications for vaccine development. Adv. Immunol. 45:195–281.

Nates, S. V., S. E. Mersich, E. B. Damonte and M. T. Zapata. 1989. Comparison of Immune response to rubella virus proteins in early and late natural infections. Microbiologica, 12:335–338.

Okuno, Y., K. Yamaniski, S. Lwin and M. Takahaski. 1985. Micro–neutralization test for mumps virus using the 96–well tissue culture plate and PAP (peroxidase–antioperoxidase) staining technique. Microbiol. Immunol. 29:327–335.

Oxford, J. S. and B. Oberg. 1985. Infections caused by rubella, reoviradae retro, norwalk, and coronavirus. In Conquest of viral disease. P. 405–438.

Pettersson, R. F., Oker–Blom, N. Kalkkinen, A. Kallio, I. Ulmanen, L. Kaariainen, P. Partanen and A. Vaheri. 1985. Molecular and antigenic characteristics and synthesis of rubella virus structural proteins. Rev. of Infect. Dis. 7:S140–149.

Preston, H. D., D. C. Miller, K. Y. Green and F. I. Byrd. 1985. Structure and function of the rubella virus proteins. Rev. of Infect. Dis. 7:S150–156.

Sandra, W. B., H. C. Stetler, S. R. Preblud, N. M. Williams, W. A. Orenstein, K. J. Bart, A. R. Hinman and K. L. Herrmann. 1985. Fetal risk associated with rubella vaccine: An update. Rev. of Infect. Dis. 7:S95–102.

Schrier, R. D., J. W. Gnann Jr, A. J. Langloes, K. Shriver, J. A. Nelson, and M. B. A. Oldstone. 1988. B–and T–lymphocyte response to an immunodominant epitope of human immunodeficiency virus. J. Virol. 62:2531–2536.

Steele, R. W., A. S. Hensen, M. M. Vincent and J. A. Bellanti. 1973. A$^{51}$Cr microassay technique for cell–mediated immunity to viruses. J. Immunol. 110:1502–1510.

Tingle, A.J., M. Allen, R.E. Petty, G.D. Kettylsand and J.K. Chantler. 1986. Rubella–associated arthritis. I. Comparative study of joint manifestations associated with natural rubella infection and RA 27/3 rubella immunization. Ann. Rheum. Dis. 45:110–114.

Van Regenmortel, M.H.V., Muller, S. Quesniaux, V.F., Altchuh, D., and J.P. Briand. 1988. Operational aspects of epitope identification: structural features of proteins recognized by antibodies. In Vaccines: New Concepts and Developments, pp. 113–122. Edited by H. Kohler and P.T. LaVerde, London: Longman.

Veskari, T. and E. Buimovici–Klein. 1975. Lymphocytes response to rubella antigens and phytohemagglutinin after administration of the RA27/3 strain of live attenuated rubella vaccine. Infect and Imm. 11:748–753.

Waxham, M. N. and J. S. Wolinsky. 1985. Detailed immunologic analysis of the structural polypeptides of rubella virus using monoclonal antibodies. Virology 143:153–165.

Virology, vol. 189, No. 2, 1992, pp. 483–492, Chaye, H et al, "Localization of the Virus Neutralizing and hemaglutinin epitopes of E1 glycoprotein of Rubella Virus", see whole document.

Journal of Virology, vol. 66, No. 11, Nov. 1992, pp. 6788–6793, Ou, D. et al. "Identification of T–cell Epitopes on E2 Protein of Rubella Virus, as recognized by human T–cell lines and Clones", see whole document.

Journal of Virology, vol. 66, No. 3, Mar. 1992, pp. 1674–1681, Ou, D. et al. "Analysis of T–and B–cell Epitopes of capsid protein of Rubella Virus by using Synthetic Peptides", see whole document.

Journal of Clinical Microbiology, vol. 30, No. 9, Sep. 1992, pp. 2323–2329, Chaye, H. H. et al., "Cellular and Humoral response to Rubella Virus structural Proteins E1, E2 and C", see whole document.

Clarke et al, "Nucleotide Sequence and in vitro Expression of Rubella Virus 24S Subgenomic Messenger RNA Encoding the Structural Proteins, $E_1$, $E_2$, and C", *Nucleic Acids Research*, vol. 5, No. 7(1987), pp. 3041–3057.

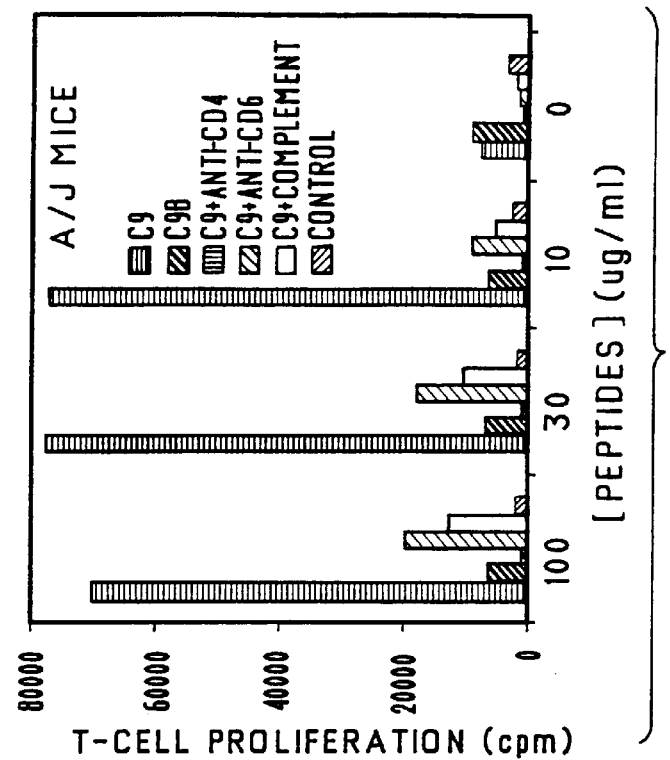
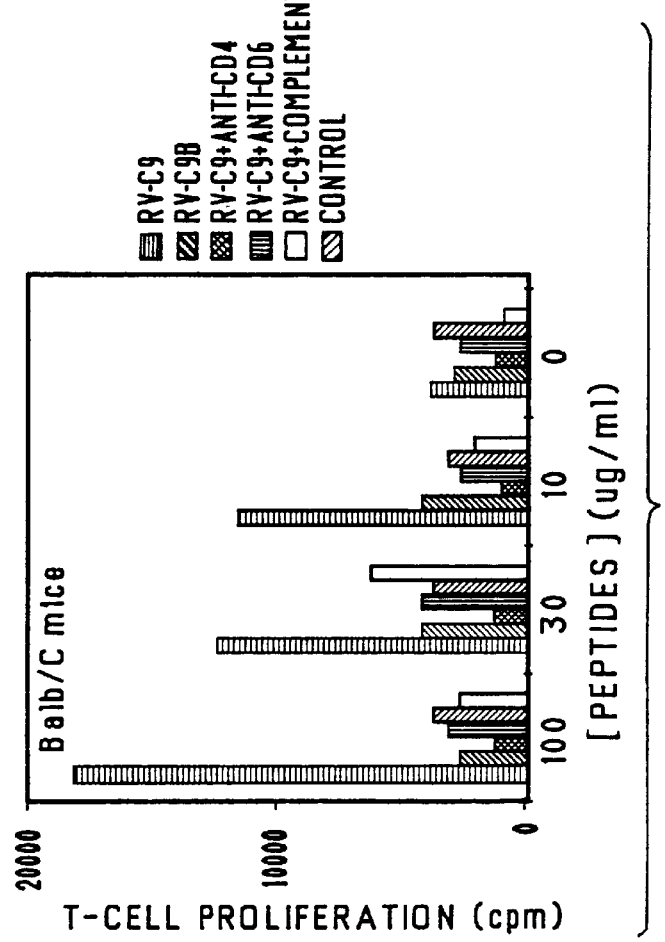

SYNTHETIC PEPTIDES FOR A RUBELLA VACCINE

This application is a Rule 371 filing of PCT/CA93/00014, filed Jan. 20, 1993.

FIELD OF INVENTION

The present invention relates to the development of synthetic vaccines against rubella viral infection. Particularly, the invention is related to the use of human T-helper determinants (THDs) and B-cell viral neutralization epitopes (BEs) from the rubella virus structural proteins E1, E2 and C, and their combination with other synthetic lipopeptides containing cytotoxic T-lymphocytes (CTL) epitopes to produce novel synthetic vaccine candidates, which can elicit neutralizing antibodies and a cell-mediated immune response against rubella virus.

BACKGROUND TO THE INVENTION

Rubella (German measles) is usually a benign childhood infection, but rubella virus (RV) can cause a persistent infection of the brain called progressive rubella panencephalitis (ref. 40,51—the literature references are listed at the end of the specification). RV has been isolated from synovial cells of some patients with juvenile rheumatoid arthritis (ref. 8,13). Several live attenuated rubella vaccines have been introduced since 1969 (ref. 2,41). Immunization of infants and susceptible women of child-bearing age against rubella virus is now a standard public health measure. However, there are serious medical concerns with the use of live attenuated rubella virus vaccine for routine immunization. These concerns include the risk of congenital infection of the fetus resulting in diabetis-related diseases (ref. 44) and rubella-associated arthritis following rubella vaccination (ref. 8,47), as well as the possibility of re-infection of vaccinees by wild-type RV due to antigenic differences between wild-type and vaccine virus strains (ref. 11,21). In addition to these problems, rubella virus grows to a relatively low titer in tissue cultures and its structural proteins are difficult to purify (ref. 27). Therefore, there is a clear requirement for preparing a non-infectious rubella vaccine by alternative means, such as recombinant DNA technology and peptides synthesis. Research efforts have recently focused on characterizing both the viral genome and the host immune responses.

RV is the sole member of the genus Rubivirus in the Togavirus family (ref. 29). The primary sequences of the rubella virus structural proteins decoded from cDNA clones have been reported (ref. 10). The RV virion contains an RNA genome enclosed within an icosahedral capsid composed of multiple copies of a basic capsid protein C of 33 kDa (ref. 38). Surrounding this nucleocapsid is a lipid bilayer in which viral glycoproteins E1 (58 kDa) and E2 (42 to 47 kDa) are embedded (ref. 38,43). Glycoprotein E1 has been shown to contain hemagglutinin and virus neutralization epitopes (ref. 50). The data accumulated to date suggest that none of the E1 neutralization epitopes is appropriate for use in a vaccine against RV since they failed to elicit high-titer neutralizing antibody responses against RV in animal studies. E2-specific antibodies are capable of neutralizing viral infection in vitro (ref. 17). However, neutralization epitopes of the E2 protein have not yet been mapped.

Studies have been carried out to characterize the specificity of the antibody response against rubella virus. The RV-specific IgM response is widely used for the diagnosis of recent rubella virus infection (ref. 19,37), and the production of RV-specific IgA antibodies has been shown to be important in the prevention of reinfection (ref. 19). Most of the RV-specific IgM antibodies react with the E1 protein while most of the IgA antibodies react with the C protein (ref. 42). IgG antibody responses can be elicited by all the structural proteins (ref. 30,42).

There is little known about the cellular immune response to RV structural proteins, although both T-helper cell proliferation (ref. 4, 22 to 24, 28, 49) and cytolytic T lymphocyte (CTL) responses (ref. 49) can be detected during viral infection. Studies cited above have neither identified the T-helper determinants nor the CTL epitopes of the rubella structural proteins. Therefore, the identification of these T-cell epitopes (T-helper and CTL) may lead to the design of a safe and effective rubella vaccine.

Methods for inducing immunity against disease are constantly improving and the current trend is to use smaller and well-defined materials as antigens. The objective is to minimize or eliminate the potential side-effects caused by certain native immunogens, while preserving both their immunogenicity and ability to confer protection against disease. Recent studies have indicated that immunization of experimental animals with synthetic peptides representing specific regions of viral or bacterial proteins can induce immune responses specific against the parent proteins, and neutralize their biological functions (ref. 3,18,25,33 to 36). Thus, synthetic peptides are potential candidate antigens for the production of inexpensive and safe vaccines against infectious diseases. Recent progress in fundamental immunology has revealed that, to be efficacious, immunogens should contain two distinct functional domains. One domain is responsible for B-cell recognition and antibody production and the second domain induce T-helper cell activity. Certainly, rubella-specific cytotoxic T-lymphocyte (CTL) epitopes should be included in the final synthetic vaccine constructs to provide necessary cellular immunity to rubella disease. A recent study (ref. 1) has demonstrated that peptides could prime mice for a CTL responses in vivo. Hence, a safe and effective synthetic peptide vaccine is conceivable.

To design a synthetic peptide-based rubella vaccine, the RV-specific CTL determinants, the viral neutralization B-cell epitopes (BE) and the functional T-helper epitopes of individual viral proteins must be identified. For a synthetic construct to be potent and efficacious, both functional T-helper and B-cell epitopes should be present. To this end, different T-B tandem synthetic peptides, both hybrid and chimeric, are synthesized to determine whether a preferential spatial relationship between T-helper determinants (THD) and B-cell epitopes in a synthetic construct is required for immunogenicity. In addition, the formulation of these synthetic constructs either with adjuvants or lipopeptides are studied to enhance immune responses.

The presentation of an appropriate processed T-cell epitope in the appropriate MHC context and the availability of an appropriate T-cell repertoire are necessary for induction of a cellular immune response. These factors vary among individuals of an outbred population and differences in T-cell responses to subunit vaccines have been reported (Zevering et al. Immunology, 2: 945–955, 1990). Other host factors, such as a possible selective T-cell tolerance to RV, also might influence antigen recognition by T-cells. Therefore, the identification of epitopes recognized by the T-cells of individuals of different genetic background and diverse immunologic experience with RV infection or immunization is important for the design of an effective synthetic vaccine.

To map the functional epitopes of rubella viral proteins, we have synthesized 28, 15 and 11 overlapping synthetic peptides covering most of the E1, E2 and C protein sequences, respectively (Tables 1, 2 and 3 below). The length of synthetic peptides was selected on the basis of their high index of hydrophilic β-turns as judged by secondary structure prediction analysis according to the conventional algorithms (ref. 9,12,20) (FIGS. 1 to 3). Such segments are likely to be surface-exposed and antigenic. Long peptides were synthesized to better mimic the native epitopes of the protein as suggested by the work of Van Regenmortel (ref. 48). An additional cysteine residue was added to either the N-terminal or the C-terminal end of the peptides for conjugation purposes.

ASPECTS OF THE INVENTION

The present invention, in one aspect, is directed towards the provision of a synthetic peptide (or a mixture of synthetic peptides) that, when administrated as a free peptide, or linked to a carrier molecule, or polymerized to form molecular aggregates, is capable of eliciting high titers of antibodies against RV in mammals.

In another aspect, the present invention is directed towards the provision of a chimeric peptide (or a mixture of chimeric peptides) that, when administrated as a free chimeric peptide, or linked to a carrier molecule, or polymerized to form molecular aggregates, is capable of inducing an immune response against RV in mammals.

The present invention, in a further aspect, is directed towards the provision of a synthetic lipopeptide (or a mixture of synthetic lipopeptides) that is capable of producing cell-mediated immunity in mammals against RV.

In an additional aspect, the present invention is directed towards the provision of a synthetic lipopeptide (or a mixture of synthetic peptides and lipopeptides) that, when forming molecular aggregates, is capable of inducing both protective antibody and cell-mediated immune responses against RV in mammals.

The present invention, in further aspect, is directed towards the provision of a synthetic peptide (or a mixture of synthetic peptides) that can be used in a diagnostic immunoassay to detect the presence of anti-RV antibodies, for example, neutralizing antibodies, and a mixture of RV-specific polyclonal antibodies that can be used in immunoassays to detect the presence of RV in a biological sample.

In yet an additional aspect, the present invention is directed towards the provision of a synthetic peptide (or a mixture of synthetic peptides) that has been identified as human THDs to generate analogs which can be used as therapeutic agents for rubella-associated autoimmune diseases.

SUMMARY OF THE INVENTION

The present invention relates to the preparation of immunogens and candidate vaccines made of peptides containing the amino acid sequences of various antigenic determinants (THDs, BEs and CTLs) of the structural proteins (E1, E2 and C) of RV. Synthetic vaccines comprising one or more of these peptides either used as free peptides, or covalently coupled to a suitable carrier, or linked to a lipidic moiety, are disclosed.

Accordingly, in one aspect of the present invention, there is provided a synthetic peptide, which may be produced by chemical synthesis or recombinantly, having an amino acid sequence corresponding to at least one antigenic determinant of at least one protein, usually a structural protein, of rubella virus (RV).

In one embodiment, the present invention comprises an essentially pure form of at least one peptide containing an amino acid sequence corresponding to at least one antigenic determinant of an E1 structural protein of RV, which peptides are capable of eliciting polyclonal antibodies against RV in mammals. These E1-specific polyclonal antibodies are useful in test kits for detecting the presence of RV in any biological sample. The peptides can have, for example, the amino acid sequences corresponding to amino acids 1–22, 19–38, 38–57, 54–74, 71–91, 105–125, 122–141, 140–159, 157–176, 174–193, 190–209, 207–226, 224–243, 240–259, 256–275, 272–291, 289–308, 307–326, 324–343, 341–360, 358–377, 374–390, 391–412, 196–212, 198–233, 219–233, 198–240 and 212–240 of the E1 protein of the RV M33 strain, respectively,as set forth in Table 1 below (SEQ ID NOS. 1 to 28), or any portion, variant or mutant thereof which retains immunogenicity.

In another embodiment, the present invention comprises an essentially pure form of at least one peptide containing an amino acid sequence corresponding to at least one antigenic determinant of an E2 structural protein of RV, which peptides are capable of eliciting polyclonal antibodies against RV in mammals, These E2-specific polyclonal antibodies are useful in test kits for detecting the presence of RV in any biological sample. The peptides can have, for example, the amino acid sequences corresponding to amino acids 15–36, 33–57, 69–91, 104–124 and 195–220 of the E2 protein of the RV M33 strain, respectively, as set forth in Table 2 below (SEQ ID NOS: 30, 31, 33, 35 and 40), or any portion, variant or mutant thereof which retains immunogenicity.

In another embodiment, the present invention comprises an essentially pure form of at least one peptide containing an amino acid sequence corresponding to at least one antigenic determinant of a C structural protein of RV, which peptides are capable of eliciting polyclonal antibodies against RV in mammals. These C-specific polyclonal antibodies are useful in test kits for detecting the presence of RV in any biological sample. The peptides can have, for example, the amino acid sequences corresponding to amino acids 1–30, 28–56, 52–78, 74–100, 96–123, 119–152, 152–179, 177–204, 205–223, 231–257 and 255–280 of the C protein of the RV M33 strain, respectively, as set forth in Table 3 below (SEQ ID NOS: 44 to 54), or any portion, variant or mutant thereof which retains immunogenicity.

In yet another embodiment, the present invention comprises an essentially pure form of a peptide containing an amino acid sequence corresponding to at least one antigenic determinant of a protein of RV, which peptide is in an oxidized form, particularly to form disulfide bridges between sulfur-containing amino acids, and is capable of eliciting a mammal to produce antibodies against RV. One such oxidized peptide has an amino acid sequence corresponding to amino acids 198–240 of the E1 protein of the RV M33 strain (Table 1, SEQ ID NO: 27–RV-EP27). Peptides of the invention also can have sequences corresponding to the analogous RV-EP27 regions of RV isolates other than M33, this sequence is designated "RV-EP27-like".

The synthetic peptides of the invention further can be either modified with lipid as lipopeptides or linked to carrier molecules (and/or polymerized to molecular aggregates) to produce alternate vaccines. Vaccines comprising the synthetic peptides provided herein or such modified forms of the peptides may be formulated as vaccines to immunize against RV infection when administered to mammals, for example, by the intramuscular or parenteral route, or when delivered to the surface mucosal surface using microparticles, capsules, liposomes and targeting molecules, such as toxins and antibodies.

Accordingly, another aspect of the present invention provides a vaccine against rubella, comprising at least one immunogenic synthetic peptide as described herein, along with a physiological carrier therefor. The vaccine may further comprise at least one other immunogenic and/or immunostimulating molecule. The immunogenic synthetic peptide may form one component of a multivalent vaccine, for example, one formulated to provide protection against measles, mumps and rubella (MMR). The vaccine may further comprise an adjuvant. The invention also includes a method of immunizing a host against rubella, by administering to the host an effective amount of the vaccine.

In another embodiment, the present invention comprises a synthetic lipopeptide (or a mixture of synthetic lipopeptides) that, is capable of inducing immune responses against RV in mammals. Such lipopeptides can have, for example, the amino acid sequence set forth in Table 12 below (SEQ ID NOS: 57 to 75), or a portion, variant or mutant thereof which retains immunogenicity. One such lipopeptide is designated TPRV-C9 and can have, for example, the sequence Tripalmityl-CSSVRAYNQPAGDVRGVWGKGERTYAEQDFRV (SEQ ID NO: 55), corresponding to amino acids 205–233 of the C protein of the RV M33 strain, or any portion thereof.

In another embodiment, the present invention comprises at least one peptide that has an amino acid sequence corresponding to at least one B-cell neutralization epitope of a protein of RV, which may be an E1, E2 or C protein, and can be used as a component of a diagnostic kit to detect the presence of anti-RV antibodies, for example, neutralizing antibodies. The peptides can have, for example, the amino acid sequences corresponding to amino acids 240–259, 256–275, 272–291, 198–233 and 212–240 of the E1 protein of the RV M33 strain, respectively, (Table 1 below, SEQ ID NOS: 14, 15, 16, 25 and 28), or any portion thereof capable of detecting the presence of RV-specific antibodies in a biological sample.

In another embodiment, the present invention comprises peptides that have been identified as human THDs (T-cell determinants). Such T-cell determinants may be those of an E1, E2 or C protein of RV. Analogs of such THDs can be used, for example, as therapeutic agents, to treat rubella-associated autoimmune disorders.

The peptides identified as human THDs can have, for example, the amino acid sequences corresponding to amino acids 1–22, 122–141, 140–159, 157–176, 174–193, 190–209, 207–226, 224–243, 240–259, 256–275, 272–291, 289–308, 307–326, 324–343, 341–360. 358–377, 374–390, 196–212, 198–233, and 198–240 of the E1 protein of the RV M33 strain, respectively, (Table 1 below, SEQ ID NOS: 1, 7, 8, 9, 10, 11, 12, 13, 14, 15, 16, 17, 18, 19, 20, 21, 22, 24, 25 and 27), or any portion thereof analogs of which are useful for therapeutic treatment of rubella-associated autoimmune disorders; the amino acid sequences corresponding to amino acids 1–20, 54–74, 139–159, 156–177, 176–199, 218–239 and 233–259 of the E2 protein of the RV M33 strain, respectively, (Table 2 below, SEQ ID NOS: 29, 32, 37, 38, 39, 41 and 42), or any portion thereof analogs of which are useful for therapeutic treatment of rubella-associated autoimmune disorders; or the amino acid sequences corresponding to amino acids 1–30, 96–123, 119–152, 151–179, 177–204, 205–233 and 255–280 of the C protein of the RV M33 strain, respectively, (Table 3 below, SEQ ID NOS: 44, 48, 49, 50, 51, 52 and 54), or any portion thereof analogs of which are useful for therapeutic treatment of rubella-associated autoimmune disorders.

In another aspect of the present invention, there is provided a method of treatment of a rubella-associated autoimmune disorder, by administering to a host an effective amount of a synthetic analog of a peptide identified as a human THD.

In another embodiment, the present invention provides a process to identify human T-cell epitopes associated with rubella-related autoimmune diseases. Such procedure involves synthesizing overlapping peptides corresponding to an RV protein, generating RV-specific T-cell lines from a panel of hosts having been exposed to RV antigens, and performing RV antigen specific T-cell proliferation assays. Results obtained from this process are used towards a rational design of synthetic peptide-based RV vaccines.

In another embodiment of the invention, the synthetic peptides comprise at least one human T-cell determinant (T) and at least one viral neutralization B-cell epitope (B), which may be in the form of hybrid or chimeric T-B tandem peptides. Such tandem peptide may be chimeric, comprising at least one human T-cell determinant of E1, E2 or C protein and at least one viral neutralization B-cell epitope of E1, E2 or C protein. Preferably, the synthetic peptide is in the form of chimeric peptide, particularly a chimeric lipopeptide, comprising at least one human T-cell determinant of E2 or C protein and at least one viral neutralization B-cell epitope of E1 protein The peptide can have, for example, sequences Tripalmityl-CSSVRAYNQPAGDVRGVWGKGER-TYAEQDFRVPDPGDLVEYIMNYTGNQQSRWGL GSP-NCHGPDWASPVCQRHSP (SEQ ID NO: 56), or any portion thereof that retains immunogenicity. Peptides of the invention can also have sequences corresponding to the analogous RV-EP27 regions of RV isolates other than M33, this sequence is designated "RV-EP27-like lipopeptide".

As mentioned above, the synthetic peptides described herein can be further either modified with lipid as lipopeptides or linked to carrier molecules (and/or polymerized to form aggregates) to produce alternate vaccines. These vaccines can be used to immunize against RV infection when administered to mammals, for example, by the intramuscular or parenteral route, or when delivered to the surface mucosal surface using microparticles, capsules, liposomes and targeting molecules, such as toxins and antibodies.

In a yet further aspect of the invention, there is provided a live vector for antigen delivery comprising a gene having a nucleotide sequence coding for an amino acid sequence of a synthetic peptide as provided herein. Such live vector may be a viral vector, such as poxviral, adenoviral, palioviral or retroviral viral vector, or a bacterial vector, such as salmonella or mycobacteria. The live vector may be provided in a vaccine against rubella with a physiologically-acceptable carrier.

BRIEF DESCRIPTION OF DRAWINGS

FIGS. 1a–b show structure prediction analysis of rubella E1 protein. The upper panel shows the secondary structure analysis of local average α-helix and β-turn potentials according to Chou and Fasman (ref. 9). The lower panel shows hydrophilicity plots according to Hopp and Woods (ref. 20). The values are derived from the average of heptapeptide windows and are plotted at the midpoint of each segment.

FIG. 2 shows structure prediction analysis of rubella E2 protein. The upper panel shows the secondary structure analysis of local average α-helix and β-turn potentials according to Chou and Fasman (ref. 9). The lower panel shows hydrophilicity plots according to Hopp and Woods (ref. 20). The values are derived from the average of heptapeptide windows and are plotted at the midpoint of each segment.

FIG. 3 shows structure prediction analysis of rubella C protein. The upper panel shows the secondary structure analysis of local average α-helix and β-turn potentials according to Chou and Fasman (ref. 9). The lower panel shows hydrophilicity plots according to Hopp and Woods (ref. 20). The values are derived from the average of heptapeptide windows and are plotted at the midpoint of each segment.

FIGS. 7a–b show proliferation response of RV-C9-specific murine T-cells to synthetic peptides, anti-CD4 antibodies and anti-CD8 antibodies. RV-C9B which is an C-terminal truncated analog of RV-C9, has amino acids sequence, VRAYNQPAGDV corresponding to residues 205–216 of C protein.

DETAILED DESCRIPTION OF THE INVENTION

The present invention relates to peptides corresponding to immunogenic epitopes of RV and synthetic vaccines made therefrom. These novel immunogenic agents are prepared by chemically synthesizing peptides sharing antigenic determinants with the structural proteins of RV. The peptides or lipopeptides are used individually or linked to carrier molecules (and/or are polymerized) as vaccines. These vaccines can be used to immunize against RV infection when administered to mammals, for example, by the intramuscular or parenteral route, or when delivered to the surface mucosal surface using microparticles, capsules, liposomes and targeting molecules such as toxins and antibodies.

Synthesis of Peptides

Figure 1A:
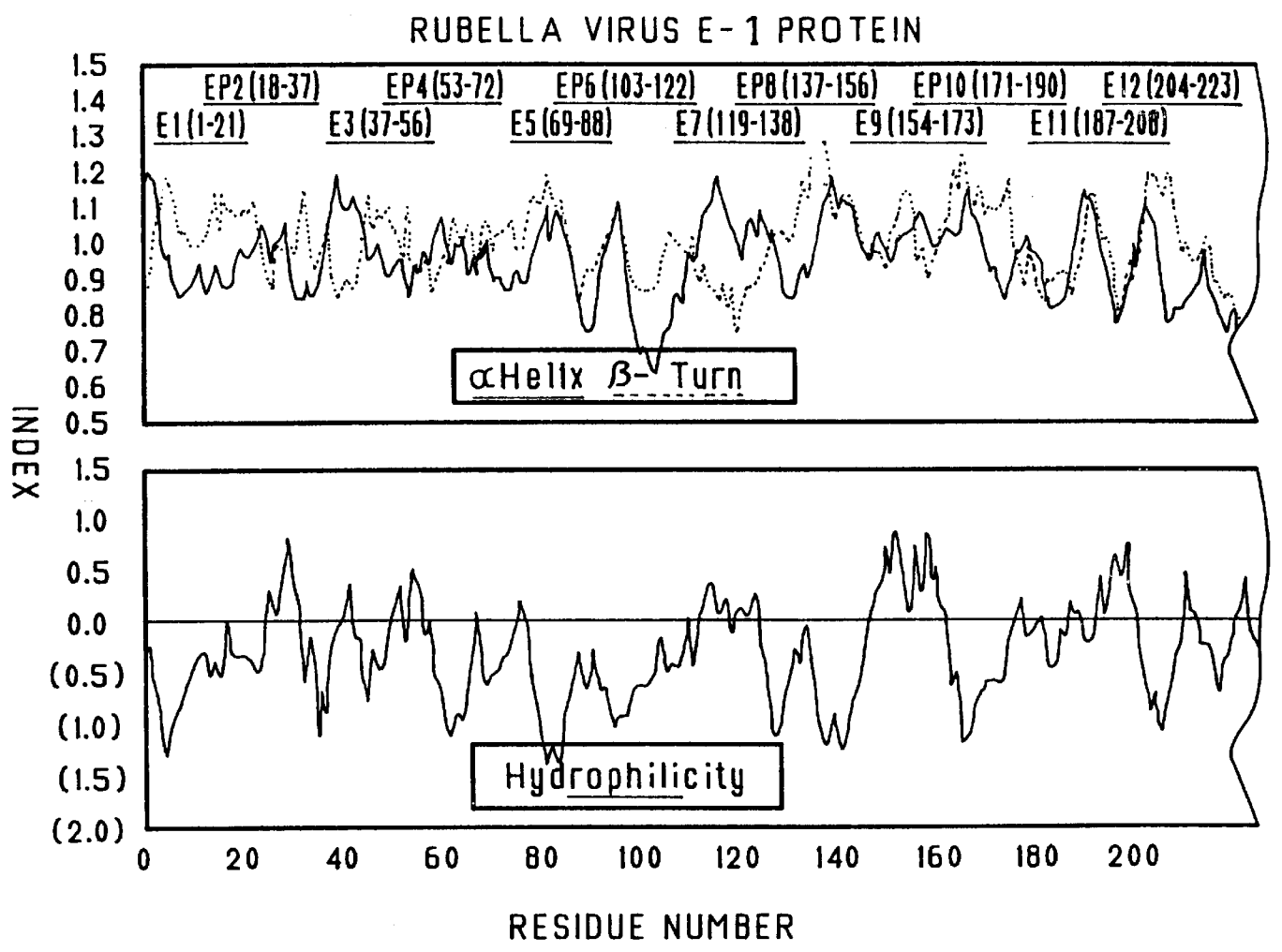
Figure 1B:
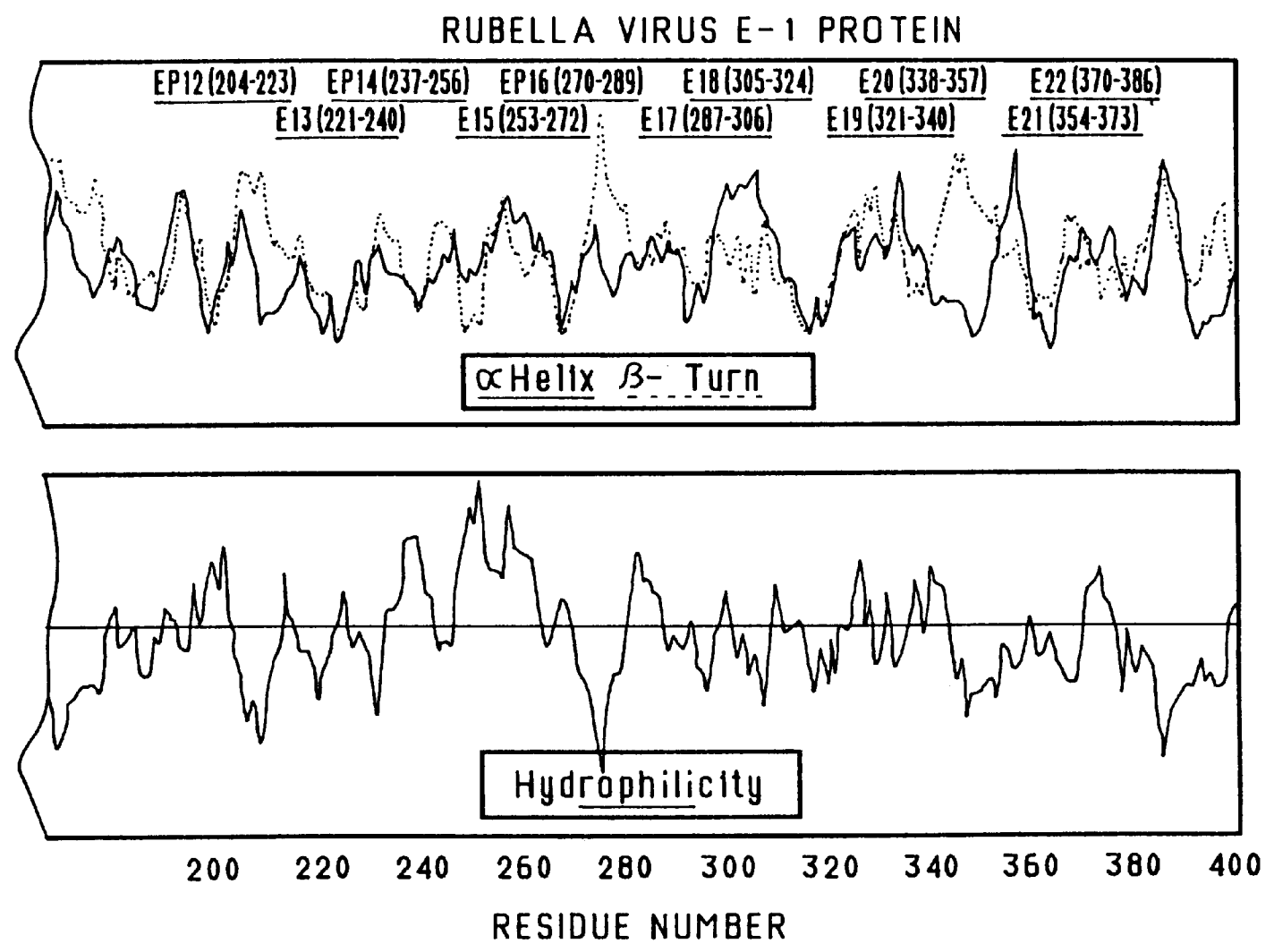
Figure 2:
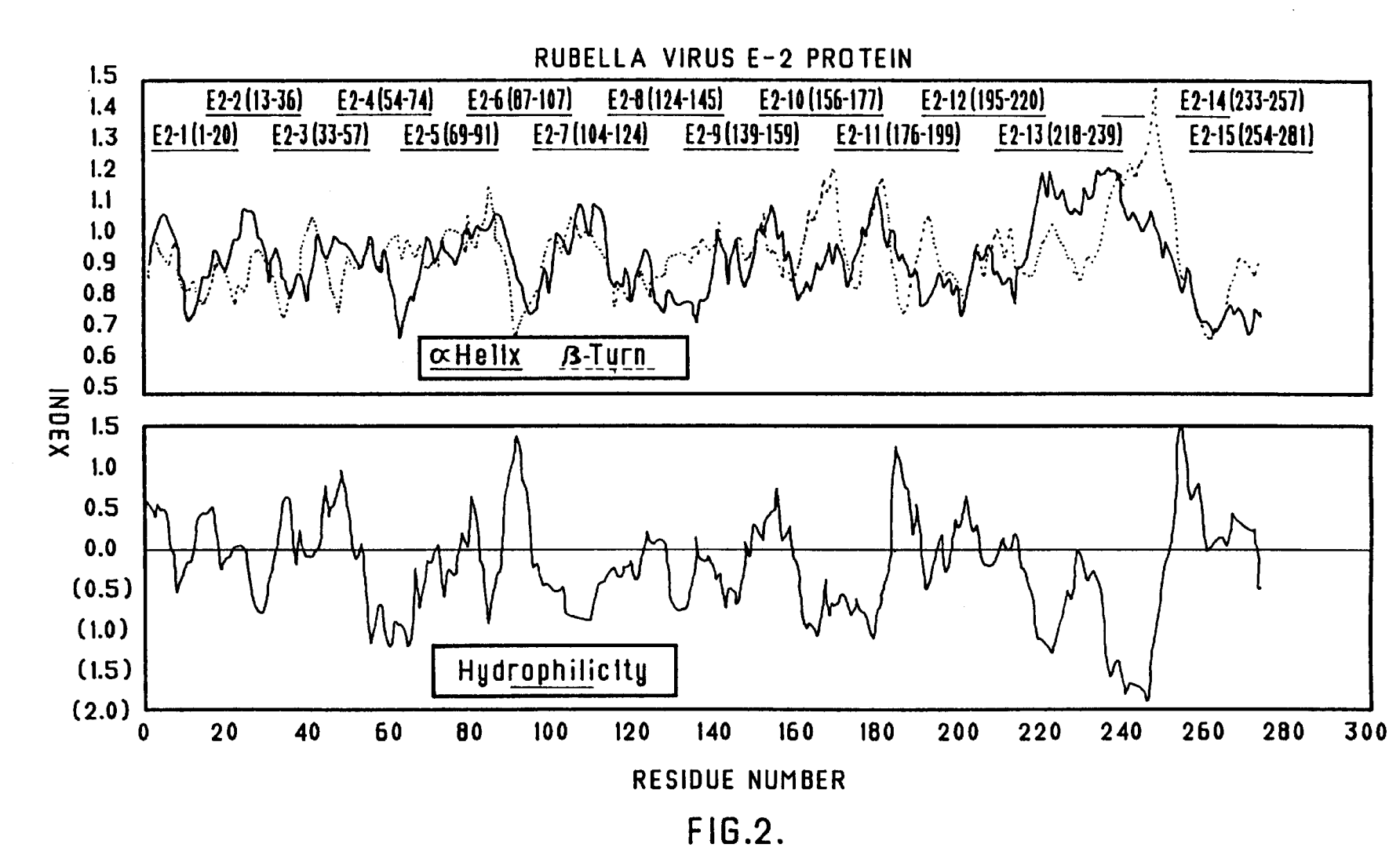
Figure 3:
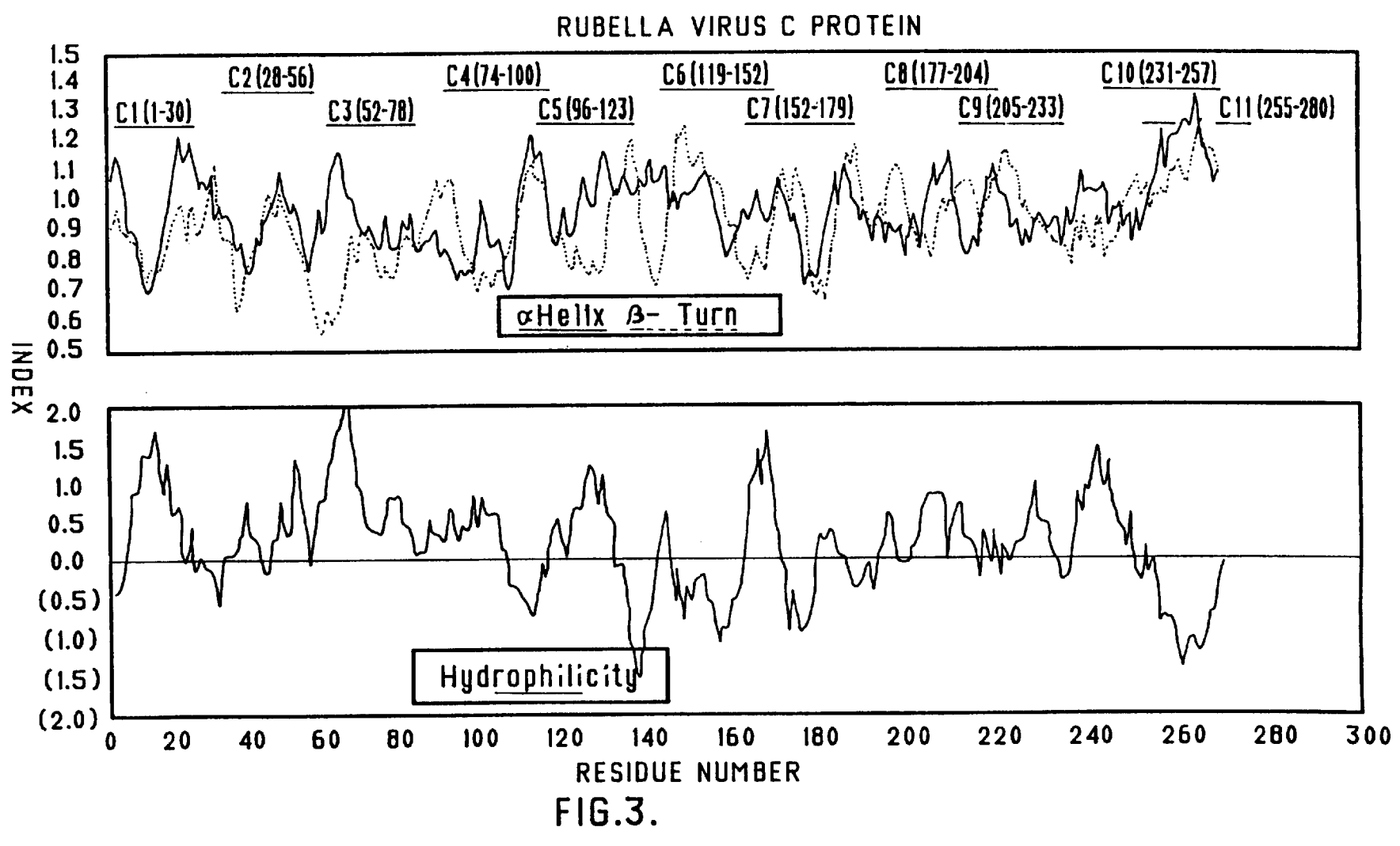

To design a synthetic peptide-based rubella vaccine, the RV-specific CTL determinants, the viral neutralization B-cell epitopes (BE) and the functional T-helper epitopes (THDs) of individual viral proteins must be identified. Fifty-four overlapping synthetic peptides covering most of the E1, E2 and C protein sequences, respectively (Tables 1, 2 and 3 below) were chemically synthesized using an automated ABI 430A solid-phase peptide synthesizer, as described in Example 2 below. The length of synthetic peptides was selected on the basis of their high index of hydrophilic β-turns as judged by secondary structure prediction analysis according to conventional algorithms (ref. 9,12,20) (FIGS. 1 to 3). Such segments are likely to be surface-exposed and antigenic. Long peptides were synthesized to better mimic the native epitopes on the protein as suggested by the work of Van Regenmortel (ref. 48). Occasionally, an additional cysteine residue was added to either the N-terminal or the C-terminal end of the peptides for conjugation purposes.

Generation and Characterization of RV-specific Monoclonal Antibodies

The production of murine RV-specific MAbs is described in Example 3 below. Antibodies were purified from ascites fluids using the Bio-Rad Affi-gel protein A MAPS II system. The subclass of the IgG monoclonal antibodies was determined by double immunodiffusion in agar using monospecific goat anti-mouse IgG subclass antisera (Tago, Burlinghams, Calif.). The results obtained are summarized in Table 4 below. The immunological properties of each MAbs were characterized by the haemagglutination inhibition (HI) and virus neutralization (VN) assays. Of the 25 monoclonal antibodies (MAbs) 3D9F, 3D5D, 12B2D and 16A10E were characterized to have HI activity of 1:16384, 1:8192, 1:4096 and 1:32, respectively (Table 4). 21B9H and 16A10E were found to have VN activity. 21B9H neutralized both the M33 and RA-27/3 strains in the presence of complement. The specificity of each MAb was determined using immunoblot analysis. The results summarized in Table 4 indicate that E1-specific MAbs such as 16A10E, 21B9H and 3D9F may be used to fine map the VN and HI epitopes of the E1 protein.

Identification of HA and VN Epitopes Using Linear Synthetic Peptides

Figure 4:
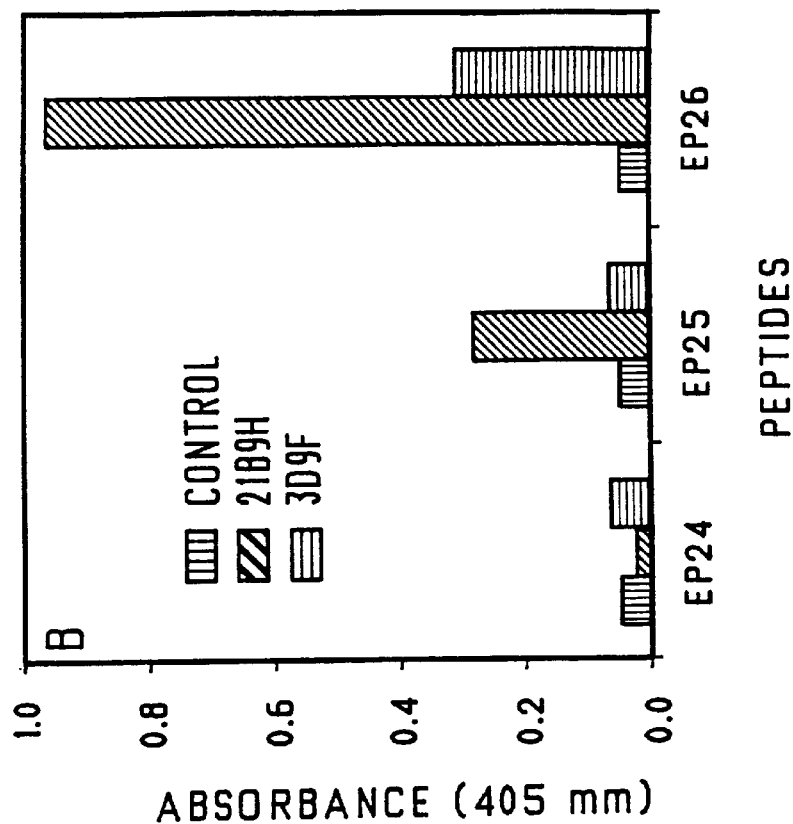
FIG. 4 comprising panels A and B, shows recognition of E1 peptides RV-EP24, -EP25, and -EP26 by MAbs 21B9H, 16A10E and 3D9F (panel A) and RV-EP24, -EP27, -EP28 by MAbs 21B9H and 3D9F (panel B). One hundred ug/mL of synthetic peptides were bound to Immulon-2 plates and probed with all MAbs except 3D9F at 1:200 dilutions of ascites fluids. Hybridoma cell culture supernatant was the source of antibody for MAb 3D9F and used at 1:50 dilution. The negative sera are normal Balb/C mouse sera not exposed to rubella.
Figure 4:
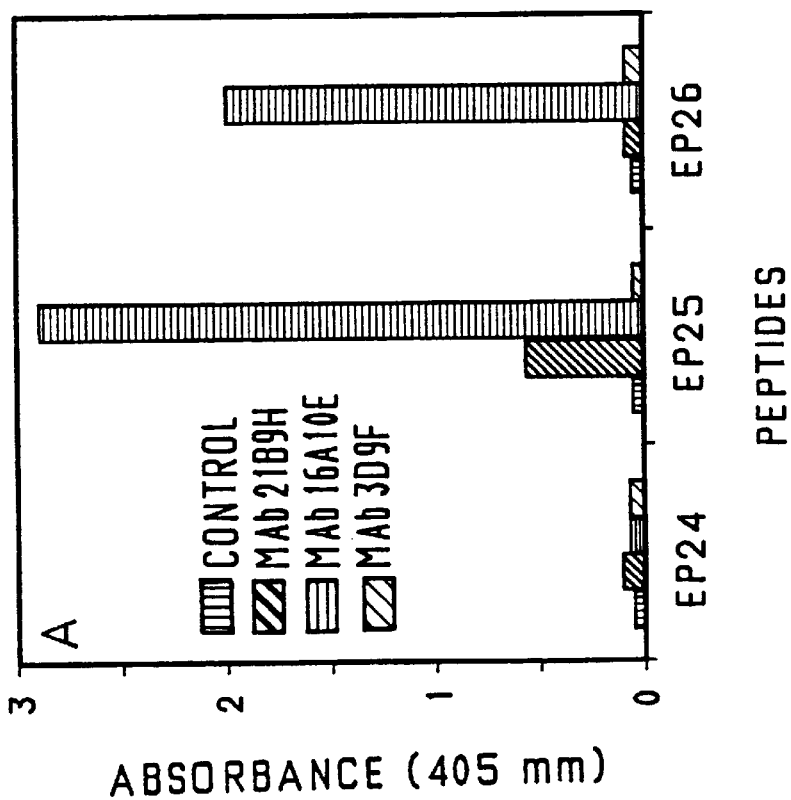

Overlapping synthetic peptides covering most of the sequence of E1 was prepared, were coated onto ELISA plates and probed with E1-specific MAbs. Although MAb 21B9H reacted strongly with RV-EP25, -EP27 and -EP28, it failed to recognize RV-EP24 and -EP26 in the peptide-specific ELISAs (FIG. 4). This results suggest that MAb 21B9H recognizes an epitope which is located in the amino acid sequence PDPGDLVEYIMNYTGNQQSRWGLGSP-NCHGPDWASP (SEQ ID NO: 25) corresponding to residues 198–233. However, another viral neutralizing MAb 16A10E reacted with both EP25 and EP26. This indicates that there is at least another neutralization epitope which is present in the amino acid sequence GLGSPNCHGPDWASP (SEQ ID NO: 26) coresponding to residues 219–233. MAb 3D9F which had strong HI activity against RV, reacted with peptide RV-EP28 corresponding to residues 212–240 (GNQQSRWGLGSPNCHGPDWASPVCQRHSP—SEQ ID NO: 28) (FIG. 4B), but not the long peptide RV-EP27. We do not know why RV-EP27 is not recognized by MAb 3D9F. In addition, two other MAbs 3D5D and 12B2D which had HI activities against RV, failed to recognize any of the synthetic peptides tested. Perhaps the hemagglutinin epitope (s) recognized by these two MAbs is conformational and could not be mimicked by linear peptides.

On the basis of the results, two conclusions can be drawn: (1) Two distinct virus neutralization epitopes were mapped to residues 198–233 (PDPGDLVEYIMNYTGNQQSRWGLGSPNCHGPDWAS P—SEQ ID NO: 25) and 219–233 (GLGSPNCHGPDWASP—SEQ ID NO: 26) as defined by their reactivity with MAbs 21B9H and 16A10E, respectively. (2) A haemagglutinin epitope defined by MAb 3D9F was mapped to residues 212–240 (GNQQSRWGLGSPNCHGPDWASPVCQRHSP—SEQ ID NO: 28).

Therefore, a mixture of peptides that comprises amino acid sequences corresponding to these E1 epitopes, can be used in a diagnostic kit to detect the presence of RV neutralizing and HI antibodies. Peptides of the instant invention can also be used in standard immunoassays to detect the presence of RV antibodies.

Immunogenicity of RV peptides

Figure 5:
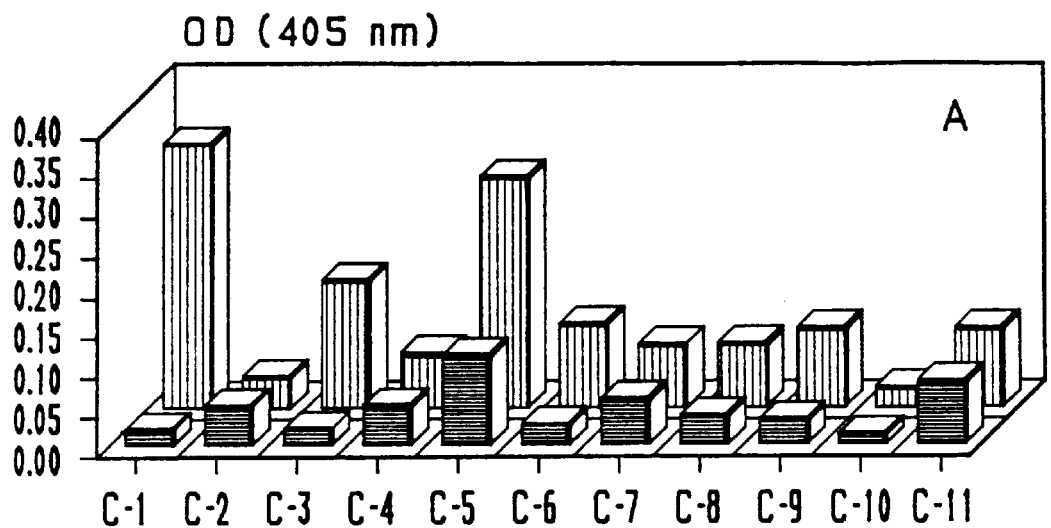
FIG. 5 comprising panels A and B, shows peptide ELISA reactivity of mouse (panel A) and rabbit (panel B) anti-capsid antisera with rubella capsid peptides.
Figure 5:
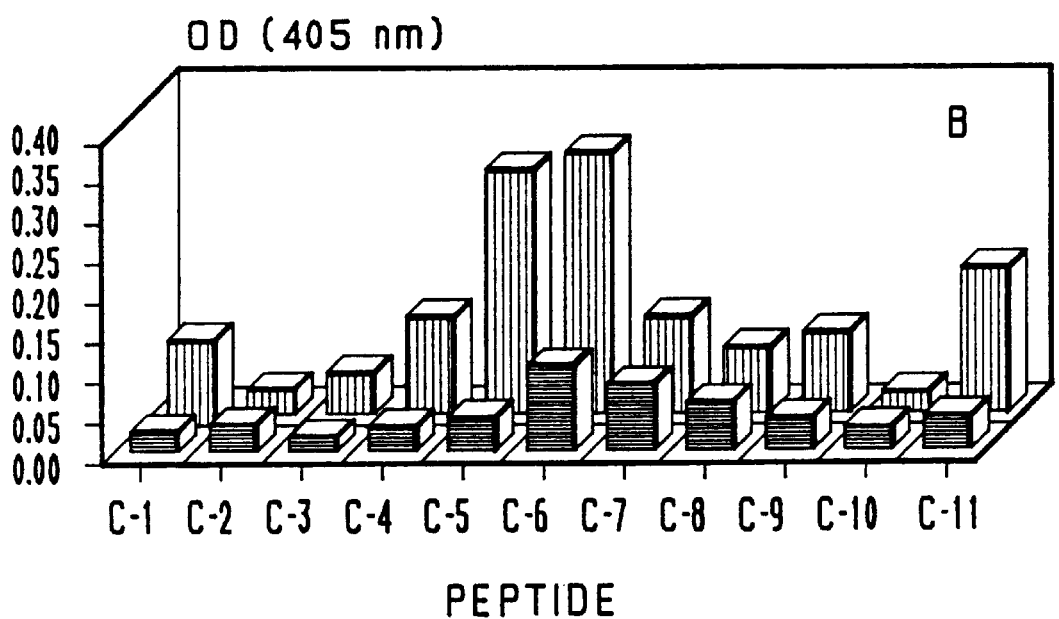
Figure 6A:
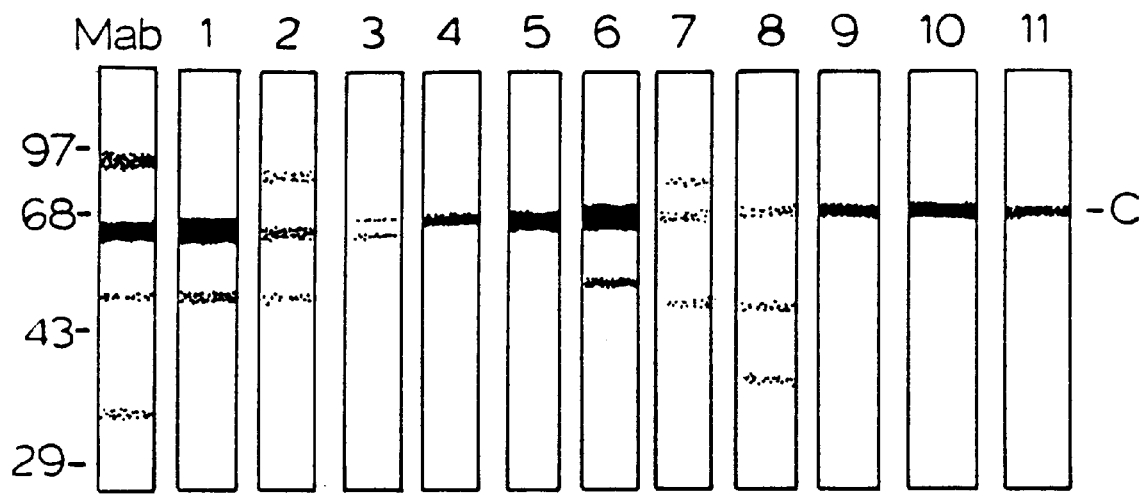
FIGS. 6a–b show immunoblot analysis of the antipeptide sera from rabbit immunized with C peptides. Immunoblot analysis was carried out under non-reducing (A) and reducing (B) conditions. Mab is the blot probed with monoclonal antibodies against C protein. The relative mobilities of protein standards (kDa) are indicated on the left. E1, E2 and C denote the structural proteins of RV. The antipeptide sera were used at a dilution 1:100.
Figure 6B:
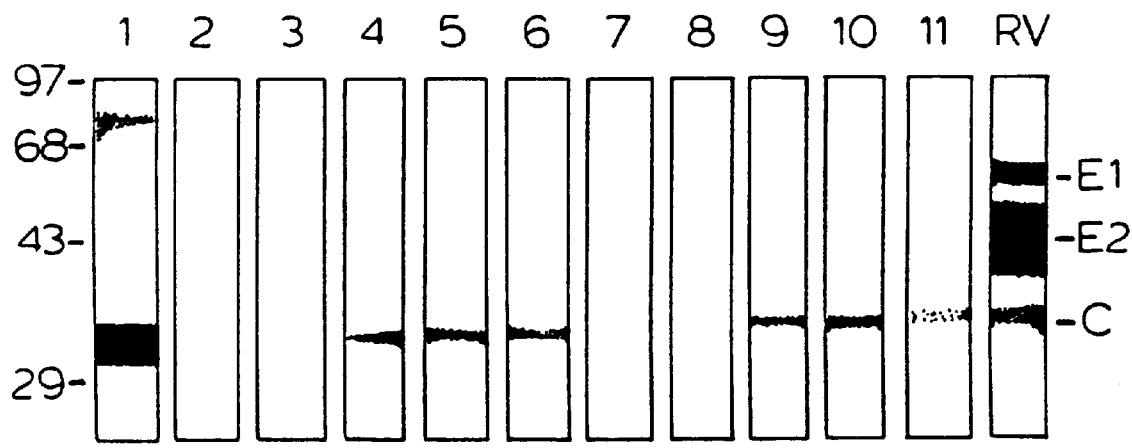

The ability of RV peptides to elicit peptide-specific antibody responses in mammals was examined by immunizing mice, guinea pigs and rabbits with individual peptides emulsified in Freund's adjuvant. After three injections (5 to 100 μg peptide per injection), IgG antibody responses were tested by peptide-specific ELISAs and immunoblotting against RV. All rabbit anti-E1 and anti-C peptide antisera reacted specifically with the immunizing peptide, and also recognized the corresponding parental protein in immunoblots (for example, see FIGS. 5 and 6). On the contrary, only certain rabbit anti-E2 peptide antisera reacted with E2 in immunoblots. These antisera were raised against E2-2, E2-3, E2-5, E2-7, and E2-12. Since free RV peptides can elicit strong IgG antibody responses, these results indicate that all synthetic peptides derived from the E1 and C proteins, as well as E2-2 (residues 15–36—SEQ ID NO: 31) E2-3 (residues 33–57—SEQ ID NO: 33), E2-5 (residues 69–91—SEQ ID NO: 35), E2-7 (residues 104–124—SEQ ID NO: 35), and E2-12 (residues 195–220—SEQ ID NO: 40) from the E2 protein comprise of both T- and B-cell epitopes. Furthermore, the presence of T-cell epitope(s) in these peptides was confirmed by human T-cell proliferation studies as described below.

Therefore, the ability of rabbit anti-RV peptide antisera to recognize RV structural proteins indicates that RV peptides (or a mixture of RV synthetic peptides) are capable of eliciting high titers of antibodies against RV in mammals. The RV-specific polyclonal antibodies raised against the peptides of the instant invention, can be used in immunoassays to detect the presence of RV in any biological sample.

Neutralization of RV by Guinea Pig Anti-E1 peptides Antisera

The immunological properties of each anti-E1 and anti-E2 peptides antisera were further characterized using haemagglutination inhibition (HI) and virus neutralization (VN) assays. All antisera raised against linear peptides failed to neutralize RV. However, guinea pig antisera raised against the oxidized form of either peptide RV-EP27 (PDPGDLVEYIMNYTGNQQSRWGLGSPNCHGPDWAS PVCQRHSP—SEQ ID NO: 27) or its N-terminal truncated analog RV-EP28 (GNQQSRWGLGSPNCHGPDWASPVCQRHSP—SEQ ID NO: 28) were capable of neutralizing M33 in the absence of complement (Table 11 below). The oxidized RV-EP28 appears to be more immunogenic than the long peptide RV-EP27. Although Terry et al. (Arch. Virol. 98: 189–197, 1988) have identified three neutralization epitopes within residues 245 to 285 of E1, none of these epitopes (RV-EP 14, residues 240–259—SEQ ID NO: 14; -EP15, residues 256–275 —SEQ ID NO: 15; and -EP16, residues 272–291—SEQ ID NO: 16) elicited neutralizing antibody responses in our studies (Table 11 below). In addition, three distinct human T-cell epitopes (RV-EP11, residues 190–209—SEQ ID NO: 11; RV-EP12, residues 207–226— SEQ ID NO: 12; and RV-EP13, residues 224–243—SEQ ID NO: 13) were identified within the RV-EP27 peptide as described below. RV-EP27 can be used as a novel vaccine candidate since it is capable of eliciting a neutralizing antibody response in mammals and contains three distinct human T-cell epitopes.

Therefore, peptides of the instant invention can have, for example, the sequence PDPGDLVEYIMNYTGNQQSR-WGLGSPNCHGPDWASPVCQRHSP (SEQ ID NO: 27), corresponding to amino acids 198–240 of E1 of the RV M33 strain, or any portion, variant or mutant thereof. Peptides of the invention also can have sequences corresponding to the analogous RV-EP27 regions of RV isolates other than M33, these sequences being designated "RV-EP27-like". Peptides described in the invention can be further either modified with lipid as lipopeptides or linked to carrier molecules (and/or polymerized) to produce alternate vaccines. These vaccines can be used to immunize against RV infection when administered to mammals, for example, by the intramuscular or parenteral route, or when delivered to the mucosal surface using microparticles, capsules, liposomes and targeting molecules, such as toxins and antibodies.

Human T-cell response to RV peptides

Human RV-specific T-cell epitopes were determined using RV peptides and T-cell lines obtained from a panel of individuals of diverse immunologic experience with RV infection or immunization. The lymphocyte proliferative responses of the RV-specific T-cell lines to overlapping E1 peptides (the first 23 peptides), E2 peptides (15 peptides) and C peptides (11 peptides) were determined in conventional proliferation assays. The results indicated that each individal in the four study groups exhibited different responses to E1, E2 and C peptides (see Tables 5 to 10 below). Not all the synthetic peptides elicited proliferative responses, and the recognition of T-cell epitopes was found to be MHC-restricted. Synthetic peptides corresponding to residues 1–22, 38–57, 54–74, 106–125, 140–159, 157–176, 174–193, 190–209, 207–226, 224–243, 240–259, 256–275, 272–291, '307–326, 324–343, 341–360, 358–377, 374–390, and 391–412 of E1; residues 1–20, 15–36, 54–74, 124–145, 156–177, 176–199, 218–239 and 233–257 of E2, and residues 1–30, 52–78, 74–100, 96–123, 119–152, 151–178, 177–204, 205–233, 231–257 and 255–280 of the C protein, when presented in the appropriate human MHC context, were shown to be highly stimulatory for RV-specific human T-cell lines. Nineteen out of 23 E1 peptides, 8 out of 15 E2 peptides and 10 out 11 C peptides were active in the proliferation assays. These results suggest that dominant T-cell epitopes are presented mainly on the E1 and C proteins, and to a lesser extent in the E2 protein.

Synthetic peptides corresponding to residues 207–226, 324–343 and 358–377 of E1, residues 54–74 of E2 and residues 119–152, 205–233 and 255–280 of the C protein were recognized by five or more human RV-specific T-cell lines. Four E1-specific T-cell clones (clones R9 and R20 specific for RVEP-10 peptide, clones R2 and R12 specific for RVEP-18), two E2-specific T-cell clones (both clones A3 and A8 specific for peptide E2–4) and nine C-specific T-cell clones (clones R5, R8, R10, R11 and R18 specific for C6 peptide; clones A2 and A11 specific for C9 peptide; clones A10 and A12 specific for C11 peptide) have been established. Three C-specific T-cell clones have cytolytic activities against various targets prepared with EBV-transformed autologous lymphoblastoid cells in the presence of RV or C protein, or peptide C6 (residues 119–151). Thus, a cytotoxic T-cell epitope was mapped to residues 119–151 of the C protein.

Delesi and Berzofsky et al. (ref. 12) proposed that T-cell epitopes were amphipathic α-helices. Rothbard and Taylor (EMBO J. 7: 93–100, 1988) suggested a different basic structure for T-cell epitope motives. A structure prediction analysis was performed with RV peptides containing functional human T-cell epitopes to determine whether their activity correlated with the presence of such structural features. We found that 5 out of 25 peptides with α-helical segments and 7 out of 29 peptides with a Rothbard's T-cell receptor-binding motif did not stimulate any of the 20 T-cell lines tested. Conversely, three peptides with no characteristic T-cell epitope structure (RV-EP19, -EP23 and E2-13) were found stimulatory. These results indicate the conventional structure prediction algorithms for T-cell epitopes are not absolute criteria for identifying T-cell determinants and that only in vitro proliferation studies can determine whether a peptide contains a functional T-cell epitope. Therefore, the identification of epitopes recognized by the T-cells of individuals of different genetic background and diverse immunologic experience with RV infection or immunization is important for the design of an effective synthetic vaccine.

Among the four subject groups tested, peptides containing human T-cell epitopes were more frequently detected in the group of healthy seropositive individuals and rubella vaccinees. Of particular interest, three of the five patients with congenital rubella syndrome (CRS) did not respond to any peptide. It is possible that in a proportion of CRS patients there is a defective T-cell recognition of RV antigen that may lead to failure or delay in the termination of RV replication, and thus may play a critical role in the persistence of the virus. In view of the increasing recognition that rubella infector or immunization may be associated with the induction of autoimmune diseases, it is possible that particular immunoreactive T-cell epitopes need to be excluded from any RV vaccine. Synthetic peptide-based RV vaccines can offer the flexibility to include of a mixture of potent human T-cell epitopes while excluding putative T-cell epitopes responsible for autoimmunity.

Immunogenicity of Lipopeptide

Generation of cell-mediated immunity (CMI) is a critical component of the immune response to RV. Nineteen lipopeptides (RV peptide modified with a lipid-linkage, N-palmitoyl-S-[2,3-bis(palmitoyloxy)-propyl]-cysteine-serine-serine) were selected from the structural proteins of RV and synthesized (Table 12 below). Some of these lipopeptides contain a CTL epitope allele-specific motif: x(Y)xxxxx(L,I,M)x or x(L,I,M)xxxxxYx (Falk et al.

Nature, 351:290, 1991; Romero et al. J Exp. Med. 174: 603–612, 1991). These RV lipopeptides were assessed for their ability to elicit peptide-specific antibody and T-cell responses in three different strains of mice with MHC H-$2^a$, H-$2^b$ and H-$2^d$ haplotypes. For example, in two strains of mice Balb/c and A/J, lipopeptides TPRV-C9 in Freund's adjuvant induced strong T-cell proliferations (FIG. 7).

RV-C9 induced RV-C9-specific antibody responses only when injected in the presence of CFA, but not with saline. By contrast, TPRV-C9 lipopeptide in saline induced strong peptide-specific IgG antibody response, although the best response was induced by priming with CFA. These results demonstrate that lipopeptides can be applied successfully to induce both T- and B-cell responses. Thus, the present invention comprises a synthetic lipopeptide (or a mixture of synthetic lipopeptides) that, is capable of inducing both humoral and cell-mediated immunity responses against RV in vivo. The lipopeptide can have, for example, the sequence Tripalmityl-CSSVRAYNQPAGDVRGVWGKGERTYAEQDFRV (SEQ ID NO: 74), corresponding to amino acids 205–233 of C protein of the RV M33 strain.

It is understood that within the scope of the invention are any variants or functionally equivalent variants of the above peptides. The terms "variant" or "functionally equivalent variant" as used above, mean that if the peptide is modified by addition, deletion or derivatization of one or more of the amino acid residues, in any respect, and yet acts in a manner similar to that of E1, E2 and C peptides for any rubella virus isolates, then it falls within the scope of the invention.

Given the amino acid sequence of these peptides (Tables 1 to 3 and 12) and any similar peptide, these are easily synthesized employing commercially available peptide synthesizers, such as the Applied Biosystems Model 430A, or may be produced by recombinant DNA technology.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. Immunological and virological methods may not explicitly described in this disclosure but are well within the scope of those skilled in the art.

EXAMPLES

Example 1

This Example illustrates the preparation of rubella virus.

The RV strain M33 (ATCC, VR-315) was grown in Vero cells and isolated from the culture supernatant as described previously (ref. 10). The virus pellets were resuspended in a small volume of PBS and stored at −70° C. The virus stock was titrated in RK 13 cells using an immunocytochemical focus assay modified from the methods described by Fukuda, Okuno and Waxham et al. (ref. 14,39,50). The virus stock ($5\times10^7$ focus forming units [FFU]/mL) was inactivated by UV-light (254 nm Model UVG-54 UV Products Inc.) for 10 minutes before use.

Example 2

This Example illustrates peptide synthesis.

Peptides were synthesized in an automated ABI 430A peptide synthesizer using the solid-phase method (ref. 31). Fifty-four peptides covering most of the sequences of rubella viral structural proteins were synthesized. In some peptides, an additional cysteine residue as indicated by the notation (C) in the Tables) was added either at the N-terminal or the C-terminal end for coupling purposes. Synthetic peptides were cleaved from the resin by HF, and purified by reversed-phase high-pressure liquid chromatography using a Vydac C4 column. The purity of all peptide preparations exceeded 95%. For all peptides, amino acid analyses were performed on a Waters Pico-Tag system and found to be in good agreement with the theoretical compositions.

Example 3

This Example illustrates generation of RV-specific monoclonal antibodies (MAbs).

Four week old Balb/C mice were immunized by intraperitoneal injection of purified rubella virus strain RA-27/3 (500 haemagglutinin (HA) units/dose/mouse) in complete Freund's adjuvant (CFA). Five 250 HA units/mouse were administered within 3 week intervals. Finally, 500 HA units/dose/mouse in saline were administered 3 days before fusion. Immune spleen cells were fused with NS-1 myeloma cells using polyethylene glycol 1500 (ref. 15). Supernatants were screened for the presence of rubella-specific antibodies by ELISA, and cells from positive wells were subsequently cloned twice by single cell dilution cloning. Each hybridoma cell line was expanded and seed stocks were stored in liquid nitrogen. Ascites were generated from mice inoculated with hybridoma cells that secreted RV-specific MAbs. Antibodies from ascites fluids were purified using the Bio-Rad Affi-gel protein A MAPS II system. The subclass of the IgG monoclonal antibodies were determined by double immunodiffusion in agar using monospecific goat anti-mouse IgG subclass antisera (Tago, Burlinghames, Calif.). Haemagglutination inhibition (HI) assays were performed using the heparin manganese chloride procedure (ref. 26). Virus neutralization (VN) was determined by plaque-assays (ref. 14).

Example 4

This Example illustrates procedure of immunization.

To prepare peptide-specific antisera, mice (Balb/C) or guinea pigs or NZW rabbits (Maple Lane Farm, Ontario) were immunized intramuscularly with 5 to 100 μg of purified peptide emulsified in Freund's complete adjuvant. Fourteen and 28 days later, animals received booster injections with the same immunogens emsulfied in incomplete Freund's adjuvant. Sera were collected two weeks after the final booster injection, heat-inactivated at 560° C., then stored at −20° C.

Example 5

This Example illustrates generation of RV-specific T cell Lines.

Peripheral blood mononuclear cells (PBMC) from RV-seropositive individuals were isolated from the heparinized blood by centrifugation through a Ficoll/Hypaque (Pharmacia LKB Biotech. Inc.) gradient as previously described (ref. 5,6). PBMCs ($2.5 \times 10^6$ cells/mL) in a 24 well plate (Gibco) were incubated with UV-inactivated RV ($5 \times 10^5$ PFU /mL) in "complete medium" (RPMI 1640 medium (Sigma) containing 2 mM L-glutamine, 25 mM Hepes, 50 mM penicillin, 50 mM streptomycin and $5 \times 10 - 5$ M 2-mercaptoethanol) supplemented with 10% autologous plasma. After incubation at 37° C. for 7 days, the cells were washed 3 times with medium and resuspended at $1 \times 10^6$ cells/mL in "complete medium" supplemented with 10% fetal calf serum (FCS) and 100 U/mL of human recombinant IL-2 (Cetus). After 7 day-incubation, an antigen-specific proliferation assay was performed.

Example 6

This Example illustrates T-cell proliferation assay.

T-lymphocytes ($2 \times 10^4$ PBMCs cells/well) from immune individuals were incubated with autologous, γ-irradiated (3000 rad) PBMCs ($5 \times 10^4$ cells/well) in complete medium containing 10% FCS and varying concentrations of antigen (individual peptides or inactivated RV) in 96-well round-bottomed plate for 3 days, as previously described (ref. 6,7). The cell cultures were pulsed with 1 μCi of [$^3$H] thymidine (DuPont) per well for the last 15–20 hours. The cells were harvested with a cell harvester (Cambridge Technology PHD) and filters were counted in a liquid scintillation counter (Beckman Le 6800). Results are presented either as the mean counts per minute (cpm) of three replicate determinations with the standard error of the mean or as the "cell proliferative index" (CPI), which is the ratio of the mean cpm incorporated in the presence of antigen to the mean cpm obtained in the absence of antigen (background). A CPI of 2 or more was considered to be statistically significant.

Example 7

This Example illustrates the generation of EBV-transformed B cell lines.

EBV-transformed B cell lines that were used as antigen-presenting cells (APCs) or target cells, were established by infection of $10^7$ PBMCs with $10^7$ PFU of EBV in 1 mL for 1 hr. at 37° C. Cells were washed and cultured in complete medium. PHA (Sigma) was added once at a concentration of 5 μg/mL, adding fresh medium every day for 2 weeks.

Example 8

This Example illustrates the generation of rubella virus-specific T-lymphocyte clones.

The T-cell clones used for this study were isolated from a $CD4^+$, $CD8^-$, T-cell line derived from a healthy male donor (RM) as described above in the Example 5. The HLA phenotype of RM was determined to be HLA-A, 2, 11; HLA-B, 13, 61, w4, w6; HLA-C w3; HLA-DR, w9, w53; HLA-DQ, w3 by the HLA Tissue Typing Laboratory of the St. Vincent's Hospital (Vancouver, B.C., Canada). RV-reactive lymphocytes were cloned by limiting dilution in 96 well round-bottom plates (Nunc) at one cell per well in the presence of UV-inactivated RV ($5 \times 10^7$ PFU/mL), 5% lymphocult-T-LF (Biotest, West Germany), 50 u/mL rIL-2 and γ-irradiated autologous PBMCs ($5 \times 10^4$/well). After 7 days of incubation, all the wells were fed with complete medium containing 5% lymphocult-T-LF and 50 u/mL rIL-2, and by day 10–12, clones of growing cells were easily identifiable with a low power inverted microscope. The cells from each one of these wells were transferred into 3 wells of a 96-well flat bottom plate, adding fresh medium with rIL-2 as described above. After 5–7 days, the cells were transferred into a single well of a 4-well plate (Nunc) with UV-inactivated RV and irradiated autologous PBMCs, and at the same time the cells were tested for antigen-reactivity in a proliferation assay.

Example 9

This Example illustrates a cell-mediated cytotoxicity assay.

Autologous EBV-transformed lymphoblastoid cells ($1 \times 10^6$) were incubated overnight at 37° C. with either $5 \times 10^7$ of UV-inactivated RV or 5 μg/mL of synthetic peptide in 1 mL of complete medium. The next day, cells were washed once and labeled with 100 μCi of $Na^{51}Cr$ (Amersham) for 1 hr. Target cells then were washed 4 times with medium and incubated with different numbers of T-cells for 4 hrs. in round-bottomed 96-well plates (Nunc). Percent specific cytotoxicity was calculated by the formula: 100 [(ER-SR) /(MR-SR)], where ER (experimental $^{51}Cr$ release)=cpm released into the supernatant in the presence of T-cells using $5 \times 10^3$ target cells in triplicate samples; SR (spontaneous $^{51}Cr$ release)=cpm in the absence of T cells determined from four replicate samples, and MR(maximal $^{51}Cr$ release)=cpm in supernatant of target cells incubated with 0.5% Nonidet-P40(Sigma) determined from four replicate samples. SR was always <20% of MR.

Example 10

This Example illustrates phenotypic analysis of T-cell surface antigens.

A short-term cultured T cells ($2 \times 10^5$) were incubated with phycoerythrin (PE)-labeled murine anti-CD3 [IOT3-PHYCO], anti-CD4 [IOT4-PHYCO], anti-CD8 [IOT8-PHYCO] monoclonal antibodies (AMAC Inc.) or normal mouse serum for 0.5 hour on ice (ref. 5). The cells were washed three times with PBS containing 5% FCS and then subjected to cytometric analysis in a fluorescence activated cell sorter (FACS) (EPICS, Coulter Electronic Co.). Pooled normal BALB/c mouse serum was used as a negative control.

Example 11

This Example illustrates peptide-specific ELISAs.

Microtiter plates (Nunc-Immuno, Nunc, Denmark) were coated with peptide (1 μg/well) in coating buffer (15 mM $Na_2CO_3$, 35 mM $NaHCO_3$, pH 9.6) overnight at room temperature as previously described (16,45). The wells were blocked with diluent (0.5% BSA, 0.5% Tween 20 in PBS) for 1 hour and serum samples (human, or rabbit or mouse antisera) were added at dilutions ranging from 1:16 to 1:2048 for one hour. The wells were washed five times with washing buffer (PBS containing 0.1% BSA and 0.5% Tween 20) and an affinity-purified, phosphatase-conjugated goat antibody to either human IgG, or mouse IgG, or rabbit IgG (KPL) was added. After one hour incubation, the plates were washed 5 times, then developed by adding 160 μL/well of p-nitrophenyl phosphate (2.5 mg/mL in 10% diethanolamine, 0.01% $MgCl_2$, pH 9.8) at 160 μL/well. After 0.5 hour, the optical density was measured at 405 nm using a Bio-Rad Microplate Reader, Model 3550. Human RV-negative serum and pre-immune rabbit serum were used as negative controls. Seropositivity for human serum was defined as any value greater than the mean of the negative control plus 3 standard deviations. Negative control values for human peptide ELISAs were established by running each peptide with a panel of negative control sera and averaging the absorbance value. Positivity was determined at a serum dilution of 1:64. Each specimen was tested at least three times.

Example 12

This Example illustrates an immunoblot analysis.

Purified rubella virus particles were subjected to SDS-PAGE on 10% polyacrylamide gels containing 0.1% SDS. After electrophoretic separation, proteins were transferred to nitro-cellulose membranes (Hybond C, Amersham). Membranes were blocked in TBS (0.15M NaCl, 0.02M Tris-HCl, pH 7.5) containing 4% powdered skimmed milk, and incubated with either human anti-RV serum (1:80 dilution) or rabbit anti-peptide serum (1:100 dilution). The proteins were visualized using peroxidase-conjugated anti-human IgG or anti-rabbit IgG antibody (Dako Corporation). Densitometric tracings on the immunoblot strips were made using a video densitometer 620 (Bio-Rad, Richmond, Calif.) and the relative density of bands was determined by integration of the areas of the absorbance peaks.

Example 13

This Example illustrates inhibition of cytotoxic and T-helper cell proliferation by Murine MAbs to human MHC class I and II antigens.

MAb L 243, specific for a DR monomorphic determinant, was obtained from Becton Dickinson. MAb G2a.5 (anti-DR DC-1, DR4, DR5), MAb IVD12 (ant- DQw3), MAb SFR-DR5 (anti-DR5), MAb w6/32 (anti-HLA A, B, C) were obtained from hybridoma cells purchased from the American Type Culture Collection.

Example 14

This Example illustrates HLA tissue typing.

HLA typing of class I and class II (DR and DQ) antigens of 20 donors was kindly performed on fresh PBMCs by the HLA Tissue Typing Laboratory of the St. Vincent's Hospital (Vancouver, B.C., Canada).

Example 15

This Example illustrates determination of rubella antigen activity.

The heparin/manganese chloride technique (26) was used for HA assays. In a 96-well round bottomed microtitre plate, 25 μL of HSAG buffer (0.025M Hepes, 0.14M NaCl, 0.025M $CaCl_2.2H_2O$, 1% BSA, 0.025 mg gelatin/L, pH 6.5) were added to 10 wells and 50 μL (cell control) into a separate well, followed by 25 μL of reconstituted rubella HA antigen into the first well, making serial doubling dilutions of the antigen. Twenty-five μL of HSAG buffer were subsequently added to all wells containing the antigen and the plates were chilled at 4° C. Fifty μL of a 0.25% (v/v) day-old chick erythrocyte suspension in HSAG buffer were added to each well. The plates were agitated, covered and left undisturbed at 4° C. for 1.5 to 2 hrs. The highest dilution exhibiting agglutination was designated as having 1 HA unit. The antigen dilution containing 4 HA units was used in all subsequent tests.

Example 16

This Example illustrates pre-treatment of sera to remove non-specific inhibitors.

Non-specific serum inhibitors of rubella virus haemagglutinin were removed by heparin treatment (ref. 26). Twenty μL of serum and 30 μL of HSAG buffer were mixed with 20 μL heparin-$MnCl_2$ solution (1M $MnCl_2$, 2500 IU/mL heparin) and incubated at 4° C. for 15 minutes followed by 20 μL of a 50% chick erythrocyte suspension in HSAG buffer, agitated and incubated at 4° C. for one hour. Eighty μL of HSAG buffer was then added and the erythrocytes pelleted by centrifugation for 15 minutes at 1500 rpm (600 g), resulting in a supernatant diluted 1:8.

Example 17

This Example illustrates determination of HI antibodies in sera (26).

Twenty-five μL of rubella antigen (4 HA units) were added to each round-bottomed wells containing 25 μL of pretreated serum that had been serially doubly diluted in HSAG buffer, and to a control well containing only 25 μL of HSAG buffer (serum control). Plates were incubated for one hour at 4° C. Fifty μL of the 0.25% (w/v) day-old chick erythrocyte suspension were added to all wells including two containing only 50 μL of HSAG buffer (cell control), followed by incubation at 4° C. for one hour, then room temperature for 15 minutes. The highest dilution of serum showing no agglutination was designated as having one HI unit, and the HI titre of the serum was calculated as the reciprocal of the dilution.

Example 18

This Example illustrates a rubella virus neutralization assay (ref. 14).

Forty μL of ascites fluid or control serum were heated at 56° C. for 20 minutes to inactivate complement, diluted 1:5 in M199 medium with 2% FCS and 1% phosphatidylserine (PS), centrifuged for 10 minutes at 10,000 rpm and sterilized by filtration through a 0.22μ pore size Gelman filter. Serial doubling dilutions of the serum were performed in M199 medium with 2% FCS/1% PS to which were added equal amounts of M33 or RA 27/3 rubella virus (2 PFU/μL, in M199 medium, 2% FCS/1% PS), with or without 2.5% rabbit complement. The virus-antibody mixture were incubated at 37° C. for one hour, then 50 μL were incubated with one-day-old RK cell monolayers in the 96 well microtitre plates, mixing for one hour at 37° C. The virus-antibody mixture were removed and the monolayers were incubated in M199 medium containing 5% FCS and 1% PS at 35° C. for 60 to 72 hours. RK cell monolayers were gently washed twice with 0.2 mL of PBS, pH 7.4, fixed with 0.2 mL 2% neutral buffered formalin for 15 minutes at room temperature, and then washed twice with 0.2 mL PBS, pH 7.4. Monolayers were then wash with 70%, then 95% methanol, and endogenous peroxidase was inactivated with 0.2 mL of 0.5% $H_2O_2$ in absolute methanol for 15 minutes at room temperature. Samples were rehydrated with 95%, then 70% methanol and washed twice with 0.2 mL PBS, pH 7.4. The non-specific immunoglobulin binding sites of the monolayers were blocked by incubation for one hour at 37° C. with 0.2 mL of pre-immune rabbit serum (diluted 1:200 in PBS/0.5% BSA) and washed twice with wash buffer (PBS, 0.1% BSA, pH 7.4). Two hundred $\mu$L of rubella immune mouse serum (anti-M33, diluted 1:200 in PBS/ 0.5% BSA), was added and incubated at 37° C. for 60 minutes followed by three wash buffer rinses. Peroxidase-conjugated (HRP) rabbit immunoglobulin anti-mouse IgG (Dako-immunoglobulins a/s, Guidborgvej 22, DK-2000 Copenhagen F., Denmark, 1:500 in PBS/0.5% BSA, 0.1 mL per well) was added and incubated for one hour at 37° C. and monolayers were rinsed three times with wash buffer. 0.1 mL of cold PBS containing 0.02% $H_2O_2$ and 3,3' diaminobenzidine tetrahydrochloride (0.5 mg/mL, pH 7.4) was applied and monolayers were incubated at room temperature. When brown deposits developed, reactions were halted by removing the substrate with a PBS rinse and adding 10% neutral buffered formalin. Plaques were enumerated from three wells per antibody dilution, and averaged. The neutralization titre (Nt) was defined as the reciprocal of the dilution that demonstrated at least a 50% reduction in plaque formation compared to control wells (50 to 100 PFU/well).

Example 19

This Example illustrates synthesis of lipopeptides.

Nineteen potential CTL epitopes of RV (see Table 12 below) were synthesized with two additional serine residues at their N-terminal end using solid-phase peptide synthesis. Lipopeptides were prepared by coupling the N-terminal end of the potential CTL epitopes with N-palmitoyl-S-[2,3-bis (palmitoyloxy)-propyl]-cysteine (P3C) which was prepared according to Metzger et al. (Int. J. Protein Res. 38: 545–554, 1991). Synthetic lipopeptides were cleaved from the resin by HF, and purified by gel filtration high-pressure liquid chromatography using a TSK column (Bio-Sil SEC125, 7.5×600 mm) using PBS as butfer. For all lipopeptides, amino acid analyses were performed on a Waters Pico-Tag system and found to be in good agreement with the theoretical compositions. The amount of palmitic acid in the lipopeptides was determined from the lipopeptide acid-hydrolysates by gas chromatography.

Example 20

This Example illustrates inductproliferatine T-cell proliferation responses by lipopeptide immunization.

Six to eight week old mice (Balb/C, C57BL/6 and A/J) were purchased from the Jackson Lab. Three mice per strain were immunized subcutaneously in foot pads with either individual lipopeptide for example, 20 to 200 $\mu$g of TPRV-C9 in 100 $\mu$L of PBS, or 20 to 200 $\mu$g of TPRV-C9 emulsifed in 100 $\mu$L of CFA, or 20 to 200 $\mu$g of TPRV-C9 emulsifed in 100 $\mu$L of incomplete Freund's adjuvant (IFA), or 100 $\mu$L of PBS:CFA (v/v, 50:50) as control. Suspensions of lymphocytes were prepared from lymph nodes removed 9 days after immunization. Lymphocytes ($2.5 \times 10^5$ cells/well) were incubated for 3 days with varying amounts of the immunizing peptide (for example RV-C9), followed by a further 20 hr incubation in the presence of 1 uCi [$^3$H]-thymidine. The effect of anti-CD4 (GK1.5) and anti-CD8 (53-6.72) MAbs on T-cell proliferation was analysed by pre-incubating lymph node cells with either anti-CD4 (GK1.5) or anti-CD8 (53-6.72) for 60 min at 4° C. in the presence and absence of rabbit complement (1:10). Lymphocyte proliferation was expressed as the average counts per minute (cpm) of triplicate determination plus/minus one standard deviation (SD).

Example 21

This Example illustrates the preparation of an oxidized form of peptide RV-EP27.

HPLC-purified RV-EP27 (5 mg in 10 mL of PBS) was oxidized in the presence of 10 to 20% (v/v) of dimethylsulfoxide (DMSO) for 1 h at room temperature according to the procedure described by Tam et al. (Proceedings of the 12th American Peptide Symposium, ESCOM, Leiden, 1992, pp. 499–501). The oxidized RV-EP27 containing the intra-chain disulfide bond ($Cys^{225}$—$Cys^{235}$) was purified by reversed-phase HPLC using a Vydac C4 semi-preparative column (1×30 cm) and a 15 to 55% acetonitrile gradient in 0.1% TFA developed over 40 min at a flow rate of 2 mL/min. The integrity of the oxidized RV-EP27 peptide was confirmed by mass spectrum analysis and the oberved molecular mass was found to agree with the calculated value.

SUMMARY OF DISCLOSURE

In summary of this disclosure, the present invention provides immunogenic synthetic peptides which are useful in vaccines against rubella. Modifications are possible within the scope of this invention.

REFERENCES

1. Aichele, P., H. Hengartner, R. M. Zinkernagel and M. Schulz. 1990. Antiviral cytotoxic T cell response induced in vivo priming with free synthetic peptide. J. Exp. Med. 171:1815–1820.
2. Assad, F., K. Ljungars-Esteves. 1985. Rubella-world impact. Rev. of Infect. Dis. 7:S29–36.
3. Barnett, B. C., D. S. Burt, C. M. Graham, A. P. Warren, J. J. Skehel and D. B. Thomas. 1989. I-Ad$^d$ restricted T-cell recognition of influenza hemagglutinin: Synthetic peptides identify multiple epitopes corresponding to antibody-binding regions of HAI subunit. J. Immunol. 143: 2663–2671.
4. Buimovici-Klein, E. and L. Z. Cooper. 1985. Cell-mediated immune response in rubella infection. Rev. of infect. Dis. 7:S123–128.
5. Celis, E., P. C. Kung and T. W. Chang. 1984. Hepatitis B virus-reactive human T lymphocyte clone: Antigen specificity and helper function for antibody synthesis. J. Immunol. 132: 1511–1516.
6. Celis, E., D. Ou and L. Otvos, Jr. 1988. Recognition of hepatitis B surface antigen by human T lymphocytes: Proliferative and cytotoxic responses to major antigenic determinant defined by synthetic peptides. J. immunol. 140: 1808–1815.
7. Celis, E., D. Ou, B. Dietzschold and H. Koprowski. 1988. Recognition of rabies and rabies-related virus by T cell derived from human vaccine recipients. J. Virol. 62: 3128–3134.

8. Chartler, J. K., D. K. Ford and A. J. Tingle. 1982. Persistent rubella infection and rubella-associated arthritis. Lancet. 1: 1323–1325.
9. Chou, P. Y. and G. D. Fasman. 1978. Empirical prediction of protein conformation. Annu. Rev. Biochem. 47: 251–276.
10. Clarke, D. M., T. W. Loo, I. Hui, P. Chong and S. Gillam. 1987. Nucleotide sequence and in vitro expression of rubella virus 24S subgenomic messenger RNA encoding the structural proteins E1, E2 and C. Nucleic Acids Research. 15: 3041–3057.
11. Cusi, M. G., G. M. Rossolimi, C. Cellesi and P. E. Valensin. 1988. Antibody response to wild rubella structural proteins following immunization with RA27/3 live attenuated virus. Arch. Virol. 101: 25–33.
12. Delisi, C. and J. A. Berzofsky. 1985. T-cell antigenic sites tend to be amphipathic structures. Proc. Natl. Acad. Sci. USA. 82: 7048–7052.
13. Fraser, J. R. E., A. L. Cunningham, K. Hayes, R. Leach and R. Lunt. 1983. Rubella arthritis in adults. Isolation of virus, cytology and other aspects of synovial reaction. Clin. Exp. Rheumatol. 1: 287–293.
14. Fukuda, A., M. Hisshiyama, Y. Umino and A. Sugiura. 1987. Immunocytochemical focus assay for potency determination of measles-mumps-rubella trivalent vaccine. J of Virological Method. 15: 279–284.
15. Galgre, G., S. Howe, C. Milstein, G. W. Butcher and J. C. Howard. 1977. Antibodies to major histocompatibility antigens produced by hybrid cell lines. Nature 266: 550–554.
16. Gnann Jr, J. W., P. L. Schwimmbeck, J. A. Nelson, A. B. Truax and M. B. A. Oldstone. 1987. Diagnosis of Aids by using a 12-amino acid peptide representing an immunodominant epitope of the human immunodeficiency virus. J of Infect. Dis. 156: 261–267.
17. Green, K. Y. and H. P. Dorsett. 1986. Rubella virus antigens: Localization of epitopes involved in hemagglutination and neutralization by using monoclonal antibodies. J. virol. 57: 893–898.
18. Green, N., H. Alexander, A. Olson, S. Alexander, T. M. Shinnick, J. G. Sutcliffe and R. A. Lerner. 1982. Immunogenic structure of the influenza virus hemagglutinin. Cell. 26: 477–487.
19. Harcourt, G. C., J. M. Best and J. E. Banatvola. 1980. Rubella specific serum and nasopharyngeal antibodies in volunteers with naturally acquired and vaccine induced immunity after intranasa challenge. J. Infect. Dis. 142: 145–155.
20. Hopp, T. P. and K. R. Woods. 1981. Prediction of protein antigenic determinants from amino acid sequence. Proc. Natl. Acad. Sci. USA. 78: 3824–3828.
21. Ho-Terry, L., A. Cohen, and P. Londesborough. 1982. Rubella virus wild-type and RA27/3 strains: a comparsion by polyacrylamide-gel electrophoresis and radioimmune precipitation. J. Med. Microbiol. 15: 393–398.
22. Ilonen, J. and A. Salmi. 1986 Comparison of HLA-DW1 and DW2 positive adherent cell in antigen presentation to heterozygous T cell lines: A low rubella antigen-specific response associated with HLA-DW2. 1986. Human Immunology. 17: 94–101.
23. Ishii, K., N. Nakazono, H. Sawada, K. Fukuda, A. Wakisaka, J. Moriuchi, Y. Nakai, T. Kano and M. Aizawa. 1981. Host factor and susceptibility to rubella virus infection: The association of HLA antigens. J. Med. Virol. 7: 287–297.
24. Kato, S., S. Muranaka, I. Takakura, M. Kimura and K. Tsun. 1982. HLA-DR antigen and the rubella-specific immune response in man. Tissue Antigen. 19: 140–145.
25. Lerner, R. A., N. Green, H. Alexander, F.-T. Liu, J. G. Sutcliffe and T. M. Shinnick, 1981. Chemically synthesized peptides predicted from the nucleotide sequence of the hepatitis B virus genome elicit antibodies reactive with the native envelope protein of Dane particles. Proc. Natl. Acad. Sci. USA 78: 3403–3407.
26. Liebhaber, H. 1970. Measurement of rubella antibody by haemagglutination. I. Variables affecting rubella haemagglutination. J. Immunol. 104: 818–825.
27. Loo, T. W., I. MacMonald, D. M. Clark, M. Trudel, A. Tingle and S. Gillam. 1986. Detection of antibodies to individual proteins of rubella virus. J. Virol. Meth. 13: 149–159.
28. Martin, R., P. Marquardt, S. O'Shea, M. Borkenstein and H, W. Kreth. 1989. Virus-specific and autoreactive T cell lines isolated from cerebrospinal fluid of a patient with chronic rubella panencephalitis. J. of Neuroimmunol. 23: 1–10.
29. Matthews, R. E. F. 1982. Classification and nomenclature of viruses. Intervirology 17: 1–199.
30. Mazancourt, A. de, M. N. Waxham, J. C. Nicolasand, J. S. Wolinsky. 1986. Antibody response to the rubella virus structural proteins in infants with the congenital rubella syndrome. J. Med. Virol. 19: 111–122.
31. Merrifield, R. B. 1969. Solid Phase peptide synthesis. Adv. Enzymol. 32: 221–296.
32. Meyer, H. M., P. D. Parkman and H. E. Hopps. 1969. Clinical characteristics of experimental infections induced by various attenuated rubella vaccines. Internal Symposium on Rubella Vaccines, London 1968. Symp Series Immunobiological Standard 11: 277–284.
33. Milich, D. R., D. L. Peterson, G. G. Leroux- Roels., R. A. Lerner and F. V. Chisari. 1985. Genetic regulation of the immune response to hepatitis B surface antigen (HBsAg): VI. T cell fine specificity. J. Immunol. 134: 4203–4211.
34. Milich, D. R., A. McLachlan, G. B. Thornton and J. L. Hughes. 1987. Antibody production to the nucleocapsid and envelope of the hepatitis B virus primed by a single synthetic T cell site. Nature. 329: 547–549.
35. Milich, D. R., J. L. Hughes, A. McLachlan, G. B. Thornton and A. Moriarty. 1988. Hepatitis B synthetic immunogen comprised of nucleocapsid T-cell sites and an envelope B-cell epitope. Proc. Natl. Acad. Sci. USA. 85: 1610–1614.
36. Milich, D. R. 1988. Synthetic T and B cell recognition sites: Implications for vaccine development. Adv. Immunol. 45: 195–281.
37. Nates, S. V., S. E. Mersich, E. B. Damonte and M. T. Zapata. 1989. Comparison of immunue response to rubella virus proteins in early and late natural infections. Microbiologica, 12: 335–338.
38. Oker-Blom, C., N. Kalkkinen, L. Kaariainen and R, F. Pettersson. 1983. Rubella virus contain one capsid protein and three envelope glycoprotein, E1. E2a and E2b. J. Virol. 46: 964–973.
39. Okuno, Y., K. Yamaniski, S. Lwin and M. Takahaski. 1985. Micro-neutralization test for mumps virus using the 96-well tissue culture plate and PAP (peroxidase-antiperoxidase) staining technique. Microbiol. immunol. 29: 327–335.
40. Oxford, J. S. and B. Oberg. 1985. Infections caused by rubella, reoviradae retro, norwalk, and coronaviruses. in Conquest of viral disease. P. 405–438.
41. Perfins, F. T., 1985. Licensed Vaccines. Rev. of Infect. Dis. 7: 573–76.
42. Pettersson, R. F., C. Oker-Blom, N. Kalkkinen, A. Kallio, I. Ulmanen, L. Kaariainen, P. Partanen and A.

Vaheri. 1985. Molecular and antigenic characteristics and synthesis of rubella virus structural proteins. Rev. of Infect. Dis. 7:S140–149.

43. Preston. H. D., D. C. Milier, K. Y. Green and F. I. Byrd. 1985. Structure and function of the rubella virus proteins. Rev. of Infect. Dis. 7:S150–156.

44. Sandra, W. B., H. C. Stetler, S. R. Preblud, N. M. Williams, W. A. Orenstein, K. J. Bart, A. R. Hinman and K. L. Herrmann. 1985. Fetal risk associated with rubella vaccine: An update. Rev. of Infect. Dis. 7:S95–102.

45. Schrier, R. D., J. W. Gnann Jr, A. J. Langloes, K. Shriver, J. A. Nelson and M. B. A. Oldstone. 1988. B-and T-lymphocyte response to an immunodominant epitope of human immunodeficiency virus. J. Virol. 62: 2531–2536.

46. Steele, R. W., A. S. Hensen, M. M. Vincent and J. A. Bellanti. 1973. A $^{51}$Cr microassay technique for cell-mediated immunity to viruses. J. Immunol. 110: 1502–1510.

47. Tingle, A. J., M. Allen, R. E. Petty, G. D. Kettylsand and J. K. Chantler. 1986. Rubella-associated arthritis. I. Comparative study of joint manifestations associated with natural rubella infection and RA 27/3 rubella immunization. Ann. Rheum. Dis. 45: 110–114.

48. Van Regenmortel, M. H. V., Muller, S., Quesniaux, V. F., Altchuh, D., and J. P. Briand. 1988. Operational aspects of epitope identification: structural features of proteins recognized by antibodies. In Vaccines: New Concepts and Developments, pp. 113–122. Edited by H. Kohler and P. T. LaVerde. London: Longman.

49. Veskari, T. and E. Buimovici-Klein. 1975. Lymphocytes response to rubella antigens and phytohemagglutinin after administration of the RA27/3 strain of live attenuated rubella vaccine. Infect and Imm. 11: 748–753.

50. Waxham, M. N. and J. S. Wolinsky. 1985. Detailed immunologic analysis of the structural polypeptides of rubella virus using monoclonal antibodies. Virology 143: 153–165.

51. Wolinsky, J. S. 1988. Rubella virus and its effect on the developing nervous system. In Virus infections and the developing nerous system, pp125–142. Edited by R. T. Johnson and G. Lyon. Kluwer Academic Publishers, Dordrecht.

TABLE 1

AMINO ACID SEQUENCES OF OVERLAPPING SYNTHETIC PEPTIDES OF RUBELLA VIRUS PROTEIN E1

| PEPTIDES | RESIDUES | SEQUENCE | SEQ ID NO: |
|---|---|---|---|
| RV-EP1 | 1-22 | EEAFTYLCTAPGCATQTPVPVR | 1 |
| RV-EP2 | 19-38 | VPVRLAGVGFESKIVDGGCF | 2 |
| RV-EP3 | 38-57 | FAPWDLEATGACICEIPTDV | 3 |
| RV-EP4 | 54-74 | PTDVSCEGLGAWVPTAPCARI | 4 |
| RV-EP5 | 71-91 | CARIWNGTQRACTFWAVNAYS | 5 |
| RV-EP6 | 106-125 | GSYYKQYHPTACEVEPAFGH | 6 |
| RV-EP7 | 122-141 | AFGHSDAACWGFPTDTVMSV | 7 |
| RV-EP8 | 140-159 | SVFALASYVQHPHKTVRVKF | 8 |
| RV-EP9 | 157-176 | VKFHTETRTVWQLSVAGVSC | 9 |
| RV-EP10 | 174-193 | VSCNVTTEHPFCNTPHGQLE | 10 |
| RV-EP11 | 190-209 | GQLEVQVPPDPGDLVEYIMN | 11 |
| RV-EP12 | 207-226 | IMNYTGNQQSRWGLGSPNCH | 12 |
| RV-EP13 | 224-243 | NCHGPDWASPVCQRHSPDCS | 13 |
| RV-EP14 | 240-259 | PDCSRLVGATPERPRLRLVD | 14 |
| RV-EP15 | 256-275 | RLVDADDPLLRTAPGPGEVW | 15 |
| RV-EP16 | 272-291 | GEVWVTPVIGSQARKCGLHI | 16 |
| RV-EP17 | 289-308 | LHIRAGPYGHATVEMPEWIH | 17 |
| RV-EP18 | 307-326 | IHAHTTSDPWHPPGPLGLKF | 18 |
| RV-EP19 | 324-343 | LKFKTVRPVALPRALAPPRN | 19 |
| RV-EP20 | 341-360 | PRNVRVTGCYQCGTPALVEG | 20 |
| RV-EP21 | 358-377 | VEGLAPGGGNCHLTVNGEDV | 21 |
| RV-EP22 | 374-390 | GEDVGAFPPGKFVTAAL | 22 |
| RV-EP23 | 391-412 | LNTPPPYQVSCGGESDRASAGH | 23 |
| RV-EP24 | 196-212 | VPPDPGDLVEYIMNYTG | 24 |
| RV-EP25 | 198-233 | PDPGDLVEYIMNYTGNQQSRWGLGSPNCHGPDWASP | 25 |
| RV-EP26 | 219-233 | GLGSPNCHGPDWASP | 26 |
| RV-EP27 | 198-240 | PDPGDLVEYIMNYTGNQQSRWGLGSPNCHGPDWASPVCQRHSP | 27 |
| RV-EP28 | 212-240 | GNQQSRWGLGSPNCHGPDWASPVCQRHSP | 28 |

TABLE 2

AMINO ACID SEQUENCES OF OVERLAPPING SYNTHETIC PEPTIDES OF RUBELLA VIRUS PROTEIN E2

| PEPTIDES | RESIDUES | SEQUENCE | SEQ ID NO: |
|---|---|---|---|
| E2-1 | 1-20 | GLQPRADMAAPPNPPQPPRA (C) | 29 |
| E2-2 | 15-36 | PQPPRAHGQHYGHHHHQLPFLG (C) | 30 |
| E2-3 | 33-57 | (C) PFLGHDGHHGGTLRVGQHHRNASDV | 31 |
| E2-4 | 54-74 | ASDVLPGHWLQGGWGCYNLSD | 32 |
| E2-5 | 69-91 | CYNLSDWHQGTHVCHTKHMDFWC | 33 |
| E2-6 | 87-107 | MDFWCVEHDRPPPPATPTSLTT | 34 |
| E2-7 | 104-124 | SLTTAANYIAAATPATAPPPC | 35 |
| E2-8 | 124-145 | CHAAGLNDSCGGFLSGCGPMRLP | 36 |

TABLE 2-continued

AMINO ACID SEQUENCES OF OVERLAPPING SYNTHETIC PEPTIDES OF RUBELLA VIRUS PROTEIN E2

| PEPTIDES | RESIDUES | SEQUENCE | SEQ ID NO: |
|---|---|---|---|
| E2-9 | 139-159 | CGPMRLPTALTPGAVGDLRAV | 37 |
| E2-10 | 156-177 | LRAVHHRPVPAYPVCCAMRWGL | 38 |
| E2-11 | 176-199 | GLPPWELVILTARPEDGWTCRGVP | 39 |
| E2-12 | 195-220 | CRGVPAHPGTRCPELVSPMGRATCSP | 40 |
| E2-13 | 218-239 | CSPASALWLATANALSLDHAFA | 41 |
| E2-14 | 233-257 | SLDHAFAAFVLLVPWVLIFMVCRRA | 42 |
| E2-15 | 254-281 | CRRACRRPAPPPPSPQSSCRGTTPPAYG | 43 |

TABLE 3

AMINO ACID SEQUENCES OF OVERLAPPING PEPTIDES OF RUBELLA VIRUS CAPSID (C) PROTEIN

| PEPTIDES | SEQUENCES | SEQ ID NO: |
|---|---|---|
| RV-C1 (1-30) | MASTTPITMEDLQKALEAQSRALRAGLAAG(C)<br>                 *--------------------RV-C1A | 44 |
| RV-C2 (28-56) | (C)AAGASQSRRPRPPRHARAQHLPEMTPAVT<br>               *--------------------RV-C2A | 45 |
| RV-C3 (52-78) | TPAVTPEGPAPPRTGAWQRKDWSRAPP(C)<br>               *--------------------RV-C3A | 46 |
| RV-C4 (74-100) | SRAPPPPEERQESRSQTPAPKPSRAPP(C)<br>              *----------------------RV-C4A | 47 |
| RV-C5 (96-123) | SRAPPQQPQPPRMQTGRGGSAPRPELGP(C)<br>              *--------------------RV-C5A | 48 |
| RV-C6 (119-152) | PELGPPTNPFQAAVARGLRPPLHDPDTEAPTEAC<br>                    *----------------RV-C6A | 49 |
| RV-C7 (151-179) | CVTSWLWSEGEGAVFYRVDLHFINLGTP<br>               *--------------------RV-C7A | 50 |
| RV-C8 (177-204) | GTPPLDEDGRWDPALMYNPCGPEPPAHV<br>               *--------------------RV-C8A | 51 |
| RV-C9 (205-233) | (C)VRAYNQPAGDVRGVWGKGERTYAEQDFRV<br>               *-------------------RV-C9A | 52 |
| RV-C10 (231-257) | FRVGGTRWHRLLRMPVRGLDGDTAPLP(C)<br>               *--------------------RV-C10A | 53 |
| RV-C11 (255-280) | PLPPHTTERIETRSARHPWRIRFGAP(C)<br>               *--------------------RV-C11A | 54 |

TABLE 4

Summary of immunochemical results obtained with monoclonal antibodies directed against the RA 27/3 vaccine and M33 wild-strain rubella virus

| | Protein Specificity | | IgG | | Neutralization | | | |
| | | | HI | sub- | M33 | | RA 27/3 | |
| | M33 | RA | M33 | class | No comp* | comp | No comp | comp |
|---|---|---|---|---|---|---|---|---|
| 2F4B | E1 | E1 | <8 | 1 | 10 | 5 | 5 | < |
| 2F12F | | E1 | <8 | 2a | < | < | < | < |
| 3D5D | ** | ** | 8192 | 2b | < | < | < | < |
| 3D9F | E1 | E1 | >16384 | 2b | < | < | < | < |

TABLE 4-continued

Summary of immunochemical results obtained with monoclonal antibodies directed against the RA 27/3 vaccine and M33 wild-strain rubella virus

| | Protein Specificity | | IgG HI | sub- | Neutralization | | | |
|---|---|---|---|---|---|---|---|---|
| | | | | | M33 | | RA 27/3 | |
| | | | | | No comp* | comp | No comp | comp |
| | M33 | RA | M33 | class | | | | |
| 4G6A | E1 | | <8 | 1 | < | < | < | < |
| 4G12E | | | 32 | 2a | 5 | < | < | < |
| 12B2D | | E1 | 4096 | 2a | 5 | 20 | NA | 5 |
| 12B3G | E1 | E1 | <8 | 2a | < | < | 5 | < |
| 13A1F | E1 | | 32 | 2b | < | < | < | < |
| 13A4H | | E1 | <8 | 2b | < | < | < | 5 |
| 13G6H | | | <8 | 1 | < | < | < | < |
| 14B1F | E1 | E1 | <8 | 1 | < | < | < | < |
| 14B3D | | | <8 | 1 | < | < | < | < |
| 15C3E | | | <8 | 2b | < | < | < | < |
| 15C11B | | | <8 | 1 | < | < | < | < |
| 16A3C | E1 | E1 | <8 | 2b | 20 | NA | 10 | NA |
| 16A10E | E1 | E1 | 32 | 1 | 5 | < | < | < |
| 16B2C | ** | ** | >16384 | 2b | < | < | < | < |
| 16B8D | ** | ** | >16384 | 2b | < | < | < | < |
| 16D9D | | | 64 | 1 | < | 10 | < | < |
| M6D11C | | | <8 | 1 | < | < | < | < |
| 21B8H | | E1 | <8 | 1 | < | < | < | 10 |
| 21B9H | | E1 | <8 | 1 | < | 5 | < | 20 |
| 21D9C | | | <8 | 2a | < | < | < | < |
| 21D10B | | | <8 | 2a | < | < | < | < |

*complement.
**precipitates both E1 and E2 glycoproteins.

TABLE 5

Proliferative responses to synthetic peptides of E1 by RV-specific T-cell lines from RV patients

| | | Cell proliferation indices[a] | | | | | | | | | |
|---|---|---|---|---|---|---|---|---|---|---|---|
| | | Rubella in pregnancy (A) | | | | | Congenital infection (B) | | | | |
| Peptide | Position | 1 | 2 | 3 | 4 | 5 | 6 | 7 | 8 | 9 | 10 |
| E1 | 1 | 1–22 | 3.7 | 2.4 | 0.98 | 1.32 | 0.92 | 1.11 | 0.89 | 0.61 | 0.63 | 0.56 |
| E1 | 2 | 18–38 | 0.5 | 1.48 | 0.4 | 0.19 | 0.75 | 0.73 | 0.64 | 0.84 | 0.17 | 0.14 |
| E1 | 3 | 38–57 | 1.6 | 0.90 | 1.2 | 0.87 | 0.71 | 0.92 | 1.10 | 0.94 | 0.76 | 0.86 |
| E1 | 4 | 54–74 | 0.9 | 1.3 | 1.1 | 1.1 | 0.69 | 0.88 | 0.54 | 0.98 | 0.65 | 1.76 |
| E1 | 5 | 71–91 | 1.2 | 1.0 | 1.2 | 1.8 | 0.72 | 0.75 | 0.68 | 0.93 | 0.82 | 1.45 |
| E1 | 6 | 106–125 | 0.8 | 1.15 | 1.3 | 0.99 | 0.72 | 0.65 | 0.78 | 0.65 | 0.79 | 0.52 |
| E1 | 7 | 122–141 | 1.8 | 0.9 | 1.2 | 1.19 | 0.72 | 0.94 | 0.84 | 0.85 | 1.05 | 0.69 |
| E1 | 8 | 140–159 | 1.4 | 0.82 | 0.8 | 0.51 | 0.63 | 0.54 | 0.72 | 0.91 | 0.87 | 0.52 |
| E1 | 9 | 157–176 | 1.2 | 1.02 | 0.9 | 0.79 | 1.01 | 0.71 | 0.66 | 0.82 | 2.05 | 0.60 |
| E1 | 10 | 174–193 | 3.6 | 0.85 | 1.3 | 1.01 | 0.58 | 0.96 | 0.85 | 1.12 | 1.59 | 0.90 |
| E1 | 11 | 190–209 | 2.1 | 3.65 | 3.6 | 0.94 | 0.56 | 0.63 | 0.79 | 0.84 | 0.88 | 6.68[b] |
| E1 | 12 | 207–226 | 1.2 | 0.98 | 1.1 | 0.94 | 0.56 | 0.58 | 0.60 | 0.70 | 1.92 | 0.64 |
| E1 | 13 | 224–243 | 1.2 | 1.13 | 1.5 | 7.76 | 0.71 | 1.03 | 0.94 | 0.54 | 1.73 | 0.89 |
| E1 | 14 | 240–259 | 0.8 | 1.13 | 1.0 | 1.26 | 0.51 | 0.89 | 0.74 | 0.81 | 0.64 | 0.58 |
| E1 | 15 | 256–275 | 0.8 | 2.23 | 1.0 | 0.91 | 0.73 | 0.64 | 0.86 | 0.83 | 1.19 | 0.99 |
| E1 | 16 | 272–291 | 3.0 | 0.98 | 1.0 | 1.48 | 0.83 | 0.76 | 0.98 | 1.02 | 3.11 | 0.69 |
| E1 | 17 | 289–308 | 1.1 | 0.72 | 0.8 | 1.10 | 0.79 | 0.58 | 0.65 | 0.65 | 1.11 | 0.44 |
| E1 | 18 | 307–326 | 3.2 | 1.01 | 1.4 | 2.2 | 0.63 | 0.62 | 0.55 | 0.67 | 0.97 | 0.61 |
| E1 | 19 | 324–343 | 1.3 | 3.7 | 1.5 | 1.23 | 0.58 | 0.89 | 0.76 | 0.82 | 0.81 | 5.63 |
| E1 | 20 | 341–360 | 0.8 | 3.0 | 1.7 | 1.06 | 0.62 | 1.02 | 0.98 | 1.08 | 0.81 | 1.38 |
| E1 | 21 | 358–377 | 1.1 | 2.4 | 1.8 | 1.55 | 0.61 | 0.82 | 0.62 | 1.06 | 3.18 | 7.45 |
| E1 | 22 | 374–390 | 1.0 | 2.9 | 2.1 | 0.94 | 1.04 | 0.54 | 0.88 | 1.17 | 1.23 | 5.47 |
| E1 | 23 | 391–412 | 1.5 | 2.3 | 1.7 | 1.44 | 0.59 | 0.74 | 0.68 | 0.97 | 1.17 | 5.94 |

[a] A total of $2 \times 10^4$ T cells from each cell line was tested for proliferative response to each synthetic peptide at a final concentration of 10 μg/mL in the presence of γ-irradiated autologous PBMC cells $5 \times 10^4$ as APC.
[b] Underlined numbers represent significant cell proliferation indices ($\geq 2$).

TABLE 6

Proliferative responses to synthetic peptides of E1 by RV-specific T-cell lines from seropositive healthy donors and RV vaccinees

| | | Cell proliferation indices[a] | | | | | | | | | |
|---|---|---|---|---|---|---|---|---|---|---|---|
| | | Seropositive healthy donors (C) | | | | | Vaccine recipients (D) | | | | |
| Peptide | Position | 11 | 12 | 13 | 14 | 15 | 16 | 17 | 18 | 19 | 20 |
| E1 | 1 | 1–22 | 0.57 | 1.32 | 0.80 | 1.92 | 0.81 | 1.36 | 1.59 | 0.78 | 1.53 | 1.13 |
| E1 | 2 | 18–38 | 0.47 | 0.51 | 0.69 | 1.17 | 0.05 | 0.14 | 0.08 | 0.25 | 0.15 | 0.02 |
| E1 | 3 | 38–57 | 0.73 | 1.34 | 1.14 | 1.73 | 0.84 | 2.55 | 1.82 | 1.12 | 1.84 | 0.96 |
| E1 | 4 | 54–74 | 0.83 | 1.42 | 0.98 | 2.25 | 0.34 | 0.64 | 1.42 | 2.23 | 1.62 | 0.98 |
| E1 | 5 | 71–91 | 0.80 | 1.57 | 0.90 | 1.40 | 0.50 | 1.92 | 1.64 | 1.19 | 1.86 | 1.01 |
| E1 | 6 | 106–125 | 1.20 | 1.61 | 0.80 | 1.80 | 1.48 | 0.72 | 1.47 | 2.19 | 1.34 | 1.26 |
| E1 | 7 | 122–141 | 0.66 | 1.94 | 0.88 | 1.62 | 0.78 | 0.56 | 1.50 | 1.38 | 1.41 | 1.02 |
| E1 | 8 | 140–159 | 0.45 | 2.71 | 0.80 | 1.47 | 0.44 | 0.35 | 1.58 | 1.10 | 0.83 | 1.42 |
| E1 | 9 | 157–176 | 0.99 | 3.30 | 1.60 | 1.56 | 0.94 | 0.80 | 1.42 | 0.85 | 1.67 | 1.46 |
| E1 | 10 | 174–193 | 0.85 | 3.34 | 3.90 | 2.53 | 1.07 | 0.85 | 1.33 | 1.15 | 1.69 | 1.42 |
| E1 | 11 | 190–209 | 0.81 | 2.62 | 2.45 | 1.27 | 1.07 | 12.7 | 1.51 | 1.10 | 3.32 | 1.14 |
| E1 | 12 | 207–226 | 0.84 | 1.97 | 0.80 | 2.36 | 0.57 | 0.48 | 1.63 | 0.87 | 1.82 | 1.23 |
| E1 | 13 | 224–243 | 1.19 | 2.93 | 1.32 | 2.03 | 0.91 | 0.49 | 1.55 | 0.83 | 2.25 | 1.65 |
| E1 | 14 | 240–259 | 0.45 | 3.42 | 0.79 | 2.69 | 1.17 | 2.73 | 0.89 | 2.13 | 1.51 | 0.95 |
| E1 | 15 | 256–275 | 0.62 | 1.73 | 0.90 | 1.46 | 0.90 | 1.01 | 1.51 | 1.47 | 1.50 | 3.18[b] |
| E1 | 16 | 272–291 | 2.48 | 1.78 | 2.85 | 1.74 | 0.22 | 0.44 | 1.79 | 2.19 | 1.26 | 1.20 |
| E1 | 17 | 289–308 | 0.75 | 1.82 | 0.77 | 1.93 | 0.79 | 0.99 | 1.16 | 1.26 | 1.68 | 1.10 |
| E1 | 18 | 307–326 | 2.62 | 3.33 | 0.82 | 1.60 | 0.62 | 0.40 | 1.37 | 2.36 | 1.37 | 1.25 |
| E1 | 19 | 324–343 | 0.87 | 2.84 | 3.15 | 2.36 | 0.64 | 9.80 | 4.84 | 1.21 | 4.58 | 0.95 |
| E1 | 20 | 341–360 | 0.95 | 3.36 | 3.47 | 2.27 | 1.45 | 7.29 | 1.37 | 0.57 | 1.75 | 1.22 |
| E1 | 21 | 358–377 | 2.19 | 3.15 | 2.40 | 2.54 | 0.73 | 6.92 | 2.40 | 2.39 | 1.44 | 2.24 |
| E1 | 22 | 374–390 | 2.98 | 1.64 | 1.58 | 1.64 | 1.07 | 10.00 | 1.41 | 0.90 | 1.84 | 1.52 |
| E1 | 23 | 391–412 | 1.17 | 2.55 | 2.20 | 1.60 | 1.52 | 8.28 | 2.03 | 1.14 | 1.39 | 1.33 |

[a]A total of $2 \times 10^4$ T cells from each cell line was tested for proliferative response to each E1 synthetic peptide at a final concentration of 10 μg/mL in the presence of γ-irradiated autologous PBMC cells as APC.
[b]Underlined numbers represent significant cell proliferation indices ($\geq 2$).

TABLE 7

Proliferative responses to synthetic peptides of E2 by RV-specific T-cell lines from RV patients

| | | Cell proliferation indices[a] | | | | | | | | | |
|---|---|---|---|---|---|---|---|---|---|---|---|
| | | Rubella in pregnancy (A) | | | | | Congenital infection (B) | | | | |
| Peptide | Position | 1 | 2 | 3 | 4 | 5 | 6 | 7 | 8 | 9 | 10 |
| E2 | 1 | 1–20 | 0.9 | 0.92 | 1.0 | 1,13 | 0.62 | 0.82 | 1.02 | 0.63 | 0.92 | 0.50 |
| E2 | 2 | 15–36 | 0.9 | 1.17 | 0.9 | 0.91 | 0.62 | 0.71 | 0.81 | 0.99 | 0.63 | 0.90 |
| E2 | 3 | 33–57 | 0.94 | 0.79 | 0.9 | 0.59 | 0.87 | 1.13 | 1.11 | 0.72 | 0.70 | 0.83 |
| E2 | 4 | 54–74 | 1.1 | 0.94 | 0.8 | 1.04 | 0.71 | 1.31 | 0.84 | 0.66 | 0.81 | 3.91[b] |
| E2 | 5 | 69–91 | 1.8 | 0.8 | 0.6 | 0.42 | 0.71 | 0.42 | 0.52 | 0.23 | 0.62 | 0.50 |
| E2 | 6 | 87–107 | 0.9 | 0.81 | 1.2 | 0.84 | 0.60 | 0.82 | 0.63 | 0.29 | 1.02 | 0.54 |
| E2 | 7 | 104–124 | 0.53 | 0.81 | 1.0 | 0.87 | 0.83 | 0.95 | 0.91 | 0.90 | 0.74 | 0.65 |
| E2 | 8 | 124–145 | 1.4 | 0.84 | 1.0 | 0.75 | 0.54 | 1.22 | 0.92 | 0.90 | 0.88 | 0.76 |
| E2 | 9 | 139–159 | 1.22 | 0.63 | 1.1 | 0.78 | 0.97 | 0.42 | 0.83 | 0.94 | 0.82 | 0.61 |
| E2 | 10 | 156–177 | 0.85 | 1.2 | 1.6 | 0.87 | 0.66 | 0.53 | 1.04 | 0.74 | 2.93 | 1.76 |
| E2 | 11 | 176–199 | 1.12 | 0.97 | 1.8 | 1.31 | 0.68 | 0.64 | 0.64 | 0.75 | 2.18 | 0.77 |
| E2 | 12 | 195–220 | 0.82 | 1.03 | 1.2 | 0.99 | 0.96 | 0.82 | 1.39 | 0.84 | 0.75 | 0.51 |
| E2 | 13 | 218–239 | 2.30 | 1.00 | 1.7 | 1.28 | 0.48 | 1.13 | 0.61 | 0.67 | 0.96 | 0.87 |
| E2 | 14 | 233–257 | 0.71 | 1.1 | 1.3 | 1.43 | 0.43 | 0.74 | 0.92 | 0.74 | 0.75 | 1.47 |
| E2 | 15 | 254–281 | 1.13 | 0.95 | 1.2 | 1.34 | 0.60 | 0.56 | 0.64 | 1.16 | 1.68 | 0.83 |

[a]A total of $2 \times 10^4$ T cells from each cell line was tested for proliferative response to each E2 synthetic peptide at a final concentration of 10 μg/mL in the presence of γ-irradiated autologous PBMC cells $5 \times 10^4$ as APC.
[b]Underlined numbers represent significant cell proliferation indices ($\geq 2$).

TABLE 8

Proliferative responses to synthetic peptides of E2 by RV-specific T-cell lines from seropositive healthy donors and vaccinees

| | | Cell proliferation indices[a] | | | | | | | | | |
|---|---|---|---|---|---|---|---|---|---|---|---|
| | | Seropositive healthy donors (C) | | | | | Vaccine recipients (D) | | | | |
| Peptide | Position | 11 | 12 | 13 | 14 | 15 | 16 | 17 | 18 | 19 | 20 |
| E2 1 | 1–20 | 7.02 | 1.17 | 1.56 | 1.70 | 0.83 | 0.80 | 1.94 | 0.78 | 2.06 | 0.98 |
| E2 2 | 15–36 | 1.13 | 0.84 | 0.54 | 1.46 | 0.87 | 9.66 | 1.90 | 1.46 | 2.09 | 1.03 |
| E2 3 | 33–57 | 0.73 | 0.91 | 0.82 | 1.36 | 0.62 | 0.56 | 1.48 | 0.73 | 1.25 | 0.84 |
| E2 4 | 54–74 | 3.50 | 0.86 | 5.60 | 2.70 | 0.93 | 17.6 | 1.80 | 0.62 | 2.06 | 1.04 |
| E2 5 | 69–91 | 0.53 | 0.83 | 1.69 | 1.23 | 0.60 | 1.03 | 0.80 | 0.61 | 0.89 | 0.56 |
| E2 6 | 87–107 | 0.76 | 0.92 | 0.87 | 1.56 | 1.01 | 1.82 | 1.67 | 0.88 | 1.08 | 1.05 |
| E2 7 | 104–124 | 0.65 | 0.93 | 1.10 | 1.70 | 0.69 | 0.48 | 0.66 | 1.18 | 1.33 | 0.87 |
| E2 8 | 124–146 | 1.29 | 0.91 | 1.25 | 2.30 | 0.59 | 1.67 | 1.20 | 1.11 | 1.45 | 0.83 |
| E2 9 | 139–159 | 0.81 | 0.84 | 1.21 | 0.91 | 0.76 | 0.84 | 1.41 | 0.95 | 1.80 | 1.03 |
| E2 10 | 156–177 | 7.01 | 0.65 | 0.92 | 2.08 | 0.86 | 1.16 | 1.53 | 0.85 | 1.12 | 0.66 |
| E2 11 | 176–199 | 3.22 | 0.73 | 1.22 | 1.97 | 1.54 | 1.15 | 1.42 | 0.76 | 3.08 | 0.91 |
| E2 12 | 195–220 | 0.32 | 1.02 | 1.45 | 1.50 | 0.93 | 1.21 | 1.56 | 0.66 | 1.95 | 0.83 |
| E2 13 | 218–239 | 1.94 | 0.74 | 2.00 | 3.12 | 0.91 | 1.48 | 2.08 | 0.65 | 2.09 | 0.69 |
| E2 14 | 233–257 | 1.21 | 0.72 | 1.27 | 2.30 | 3.65 | 2.37 | 1.61 | 0.51 | 1.61 | 0.84 |
| E2 15 | 254–281 | 0.75 | 0.88 | 1.07 | 1.97 | 1.65 | 1.44 | 0.63 | 0.61 | 1.38 | 1.10 |

[a]A total of 2 × 10$^4$ T cells from each cell line was tested for proliferation response to each E2 synthetic peptide at the final concentration of 10 μg/mL in the presence of γ-irradiated autologous PBMC cells as APC.
Underlined numbers represent significant cell proliferation indices ($\geq 2$).

TABLE 9

Proliferative responses to synthetic peptides of capsid protein by RV-specific T-cell lines from RV patients

| | | Cell proliferation indices[a] | | | | | | | | | |
|---|---|---|---|---|---|---|---|---|---|---|---|
| | | Rubella in pregnancy (A) | | | | | Congenital infection (B) | | | | |
| Peptide | Position | 1 | 2 | 3 | 4 | 5 | 6 | 7 | 8 | 9 | 10 |
| C1 | 1–30 | 2.0 | 7.8 | 1.1 | 1.53 | 0.60 | 1.02 | 0.80 | 0.67 | 1.05 | 0.42 |
| C2 | 28–56 | 1.2 | 1.46 | 1.4 | 1.01 | 0.93 | 0.92 | 0.80 | 1.07 | 1.71 | 0.97 |
| C3 | 52–78 | 0.97 | 1.40 | 1.0 | 1.32 | 1.63 | 1.10 | 0.84 | 0.90 | 0.72 | 1.52 |
| C4 | 74–100 | 0.72 | 1.40 | 1.5 | 1.32 | 0.74 | 0.85 | 0.83 | 0.76 | 0.61 | 0.80 |
| C5 | 96–123 | 1.1 | 1.9 | 1.7 | 1.34 | 0.71 | 0.66 | 1.02 | 0.99 | 0.98 | 2.31 |
| C6 | 119–152 | 1.48 | 2.0 | 3.7 | 2.10 | 0.86 | 0.85 | 1.22 | 0.95 | 1.73 | 2.50 |
| C7 | 151–179 | 2.7 | 1.5 | 4.1 | 5.2 | 0.76 | 1.32 | 0.60 | 0.80 | 1.73 | 6.15 |
| C8 | 177–204 | 1.2 | 1.8 | 1.2 | 3.4 | 0.89 | 1.32 | 0.50 | 1,09 | 0.96 | 0.74 |
| C9 | 205–233 | 2.82 | 4.7 | 1,9 | 4.5 | 0.62 | 1.13 | 0.80 | 1.64 | 0.85 | 0.61 |
| C10 | 231–257 | 1.24 | 1.1 | 1.4 | 1.9 | 0.72 | 0.84 | 0.80 | 0.81 | 1.34 | 1.52 |
| C11 | 255–280 | 0.95 | 3.7 | 1.4 | 2.7 | 0.81 | 1.23 | 0.70 | 1.01 | 2.10 | 2.09 |

[a]A total of 2 × 10$^4$ T cells from each clone was tested for proliferation response to each synthetic C peptide at a final concentration of 10 μg/mL in the presence of γ-irradiated autologous PBMC cells 5 × 10$^4$ as APC.
Underlined numbers represent significant cell proliferation indices ($\geq 2$).

TABLE 10

Proliferative responses to synthetic peptides of capsid protein by RV-specific T-cell lines from seropositive healthy donors and vaccinees

| | | Cell proliferation indices[a] | | | | | | | | | |
|---|---|---|---|---|---|---|---|---|---|---|---|
| | | Seropositive healthy donors (C) | | | | | Vaccine recipients (D) | | | | |
| Peptide | Position | 11 | 12 | 13 | 14 | 15 | 16 | 17 | 18 | 19 | 20 |
| C1 | 1–30 | 0.64 | 1.52 | 1.20 | 0.93 | 1.02 | 0.63 | 1.69 | 0.49 | 2.11 | 0.38 |
| C2 | 28–56 | 0.62 | 1.37 | 1.01 | 1.01 | 1.13 | 1.14 | 1.94 | 0.52 | 1.45 | 1.01 |
| C3 | 52–78 | 1.50 | 1.05 | 0.92 | 1.02 | 1.44 | 2.23 | 1.10 | 0.69 | 1.42 | 0.02 |
| C4 | 74–100 | 1.01 | 1.10 | 1.54 | 1.04 | 1.11 | 0.75 | 2.28 | 0.66 | 1.42 | 1.13 |
| C5 | 96–123 | 1.43 | 2.34 | 2.62 | 0.92 | 1.12 | 2.71 | 2.98 | 0.71 | 2.47 | 1.14 |
| C6 | 119–152 | 1.14 | 13.9 | 8.13 | 1.00 | 1.32 | 2.03 | 3.75 | 2.47 | 3.32 | 1.29 |
| C7 | 151–179 | 0.62 | 0.92 | 1.03 | 1.54 | 1.05 | 3.29 | 2.67 | 0.59 | 1.88 | 1.11 |
| C8 | 177–204 | 0.91 | 1.24 | 0.94 | 0.91 | 1.43 | 1.03 | 1.23 | 0.71 | 1.55 | 1.06 |
| C9 | 205–233 | 1.14 | 0.82 | 3.95 | 0.90 | 0.81 | 20.4 | 3.13 | 4.31 | 1.54 | 0.87 |
| C10 | 231–257 | 0.63 | 0.75 | 1.32 | 0.94 | 0.72 | 4.00 | 0.99 | 1.34 | 1.30 | 1.01 |
| C11 | 255–280 | 0.60 | 6.24 | 5.04 | 4.01 | 8.24 | 22.5 | 2.20 | 4.42 | 1.29 | 1.57 |

[a]A total of $2 \times 10^4$ T cells from each clone was tested for proliferation response to each synthetic peptide at a final concentration of 10 μg/mL in the presence of γ-irradiated autologous PBMC cells $5 \times 10^4$ as APC.
Underlined numbers represent significant cell proliferation indices ($\geq 2$).

TABLE 11

Immunological properties of animal antisera raised against RV peptides

| Immunogens | Reactive titer against peptides[1] | VN titer[2] | HI titer[3] |
|---|---|---|---|
| RV-EP14 + CFA | +++ | 0 | ND |
| RV-EP15 + CFA | +++ | 0 | ND |
| RV-EP16 + CFA | +++ | 0 | ND |
| RV-EP25 + CFA | ++++ | 0 | ND |
| RV-EP27 + CFA | +++++ | 0 | ND |
| RV-EP27 + alum | ++++ | 0 | ND |
| RV-EP27[4] + CFA | +++++ | 1/160 | ND |
| RV-EP27[4] + alum | ++++ | ND | ND |
| RV-EP28 + CFA | +++++ | 0 | ND |
| RV-EP28 + alum | ++++ | 0 | ND |
| RV-EP28[4] + CFA | +++++ | 1/320 | ND |
| RV-EP28[4] + alum | ++++ | ND | ND |

[1]+++, ++++, and +++++ are average reactive titers of anti-peptide antisera determined by peptide-specific ELISAs at 1/5,000, 1/20,000, and >1/100,000, respectively.
[2]The viral neutralization titer are determined by plaque assay without complement.
[3]The haemaggultinin inhibition assay was not done at the present time.
[4]Both peptides RV-EP27 and -EP28 were the oxidized form containing $Cys^{225}$ and $Cys^{235}$ intra-disulfide bridge.

TABLE 12

AMINO ACID SEQUENCE OF LIPOPEPTIDES

| Lipopeptides | Sequences | SEQ ID NO: |
|---|---|---|
| TPRV-EP1 | Tripalmitoyl-CSSEEAFTYLCTAPGCATQTPVPVR | 57 |
| TPRV-EP6 | Tripalmitoyl-CSSGSYYKQYHPTACEVEPAFGH | 58 |
| TPRV-EP8 | Tripalmitoyl-CSSSVFALASYVQHPHKTVRVKF | 59 |
| TPRV-EP12 | Tripalmitoyl-CSSIMNYTGNQQSRWGLGSPNCH | 60 |
| TPRV-EP17 | Tripalmitoyl-CSSLHIRAGPYGHATVEMPEWIH | 61 |
| TPRV-EP19 | Tripalmitoyl-CSSLKFKTVRPVALPRALAPPRN | 62 |
| TPRV-EP21 | Tripalmitoyl-CSSVEGLAPGGGNCHLTVNGEDV | 63 |
| TPRV-EP25 | Tripalmitoyl-CSSPDPGDLVEYIMNYTGNQQSRRWGLGSPNCHGPDWASP | 64 |
| TPRV-EP27 | Tripalmitoyl-CSSPDPGDLVEYIMNYTGNQQSRWGLGSPNCHGPDWASPCQRHSP | 65 |
| TPE2-2 | Tripalmitoyl-CSSPQPPRAHGQHYGHHHHQLPFLGC | 66 |
| TPE2-4 | Tripalmitoyl-CSSASDVLPGHWLQGGWGCYNLSD | 67 |
| TPE2-5 | Tripalmitoyl-CSSCYNLSDWHQGTHVCHTKHMDFWC | 68 |
| TPE2-7 | Tripalmitoyl-CSSSLTTAAANYIAAATPATAPPC | 69 |
| TPE2-10 | Tripalmitoyl-CSSLRAVHHRPVPAYPVCCAMRWGL | 70 |
| TPRV-C6 | Tripalmitoyl-CSSPELGPPTNPFQAAVARGLRPPLHDPDTEAPTEAC | 71 |
| TPRV-C7 | Tripalmitoyl-CSSCVTSWLWSEGEGAVFYRVDLHFINLGTP | 72 |
| TPRV-C8 | Tripalmitoyl-CSSGTPPLDEDGRWDPALMYNPCGPEPPAHV | 73 |
| TPRV-C9 | Tripalmitoyl-CSSCVRAYNQPAGDVRGVWGKGERTYAEQDFRV | 74 |
| TPRV-C11 | Tripalmitoyl-CSSPLPPHTTERIETRSARHPWRIRFGAPC | 75 |

The potential CTL epitopes are highlighted by italic letters.

What we claim is:

1. A synthetic peptide having an amino acid sequence of a portion of an E1, E2 or C protein of rubella virus (RV) and which contains a human T-cell determinant, wherein said amino acid sequence is at least one selected from:

(a) any of the amino acid sequences 1 to 22 (SEQ ID NO: 1), 38 to 57 (SEQ ID NO: 3), 54 to 74 (SEQ ID NO: 4), 106 to 125 (SEQ ID NO: 6), 140 to 159 (SEQ ID NO: 8), 157 to 176 (SEQ ID NO: 9), 174 to 193 (SEQ ID NO: 10), 190 to 209 (SEQ ID NO: 11), 207 to 226 (SEQ ID NO: 12), 224 to 243 (SEQ ID NO: 13), 240 to 250 (SEQ ID NO: 14), 256 to 275 (SEQ ID NO: 15), 272 to 291 (SEQ ID NO: 16), 307 to 326 (SEQ ID NO: 18), 324 to 343 (SEQ ID NO: 19), 341 to 360 (SEQ ID NO: 20), 358 to 377 (SEQ ID NO: 21), 374 to 390 (SEQ ID NO: 22), 391 to 412 (SEQ NO: 23) 196 to 212 (SEQ ID NO: 24) , 198 to 233 (SEQ ID NO: 25) 219 to 233 (SEQ ID NO: 26), 198 to 240 (SEQ ID NO: 27), and 212 to 240 (SEQ ID NO: 28) of E1 protein, set forth in Table 1, (b) any of the amino acid sequences 1 to 20 (SEQ ID NO: 29), 15 to 36 (SEQ ID NO: 30), 124 to 145 (SEQ ID NO: 36), 156 to 177 (SEQ ID NO: 38), 176 to 199

(SEQ ID NO: 39), 218 to 239 (SEQ ID NO: 41) and 233 to 257 (SEQ ID NO: 42) of E2 protein, set forth in Table 2, and (c) any of the amino acid sequences 1 to 30 (SEQ ID NO: 44), 52 to 78 (SEQ ID NO: 46), 74 to 100 (SEQ ID NO: 47), 96 to 123 (SEQ ID NO: 48), 119 to 152 (SEQ ID NO: 49), 151 to 179 (SEQ ID NO: 50), 177 to 204 (SEQ ID NO: 51), 205 to 233 (SEQ ID NO: 52), 231 to 257 (SEQ ID NO: 53) and 255 to 280 (SEQ ID NO: 54) of C protein, set forth in Table 3.

2. The synthetic peptide of claim 1 in an oxidized form and which is capable of eliciting a mammal to produce neutralizing antibodies against RV.

3. The synthetic peptide of claim 2 wherein said oxidized form has at least one disulfide bond between sulfur-containing amino acids.

4. The synthetic peptide of claim 1 modified with lipid to be in the form of a lipopeptide.

5. A synthetic peptide having an amino acid sequence of a portion of an E1, E2 or C protein of rubella virus (RV) and which contains a human T-cell determinant and which is modified with lipid to be in the form of a synthetic lipopeptide or a mixture of synthetic lipopeptides that, when used to form molecular aggregates, is capable of inducing mammals to produce immune responses against RV, wherein said synthetic lipopeptide is selected from those having the amino acid sequence set forth in Table 12.

6. The synthetic peptide of claim 1 wherein said selected amino acid sequence includes at least one virus neutralization epitope and/or haemagglutination inhibition epitope.

7. The synthetic peptide of claim 1 an analog of which is useful in the treatment of rubella-associated autoimmune disorders.

8. The synthetic peptide of claim 1 comprising at least one human T-cell determinant (T) and at least one viral neutralization B-cell epitope (B).

9. The synthetic peptide of claim 8 in the form of a hybrid or chimeric T-B tandem peptide.

10. The synthetic peptide of claim 8 in the form of a chimeric peptide comprising at least one human T-cell determinant of E1, E2 or C protein and at least one viral neutralization B-cell epitope of E1, E2 or C protein.

11. The synthetic peptide of claim 10 in the form of a chimeric lipopeptide.

12. The synthetic peptide of claim 11 in the form of a chimeric lipopeptide comprising at least one human T-cell determinant of E2 or C protein and at least viral neutralization B-cell epitope of E1 protein.

13. A synthetic peptide in the form of a chimeric lipopeptide comprising at least one human T-cell determinant of E2 or C protein and at least one viral neutralization B-cell epitope of E1 protein and having the amino acid sequence tripalmityl-CSSVRAYNQPAGDVRGVWGKGERTYAEQDFRVPDPGDLVEYIMNYTGNQQSRWGLGSP-NCHGPDWASPVCQRHSP (SEQ ID NO: 56), or any portion, variation or mutant thereof which retains the immunogenicity of said sequence.

14. The synthetic peptide claimed in any one of claims 1 to 3, 4, 5, 6, and 7, to 13, which is produced by chemical synthesis or by recombinant procedure.

15. A synthetic peptide having an amino acid sequence of a portion of an E1, E2 or C protein of rubella virus (RV) and which contains a human T-cell determinant.

16. The synthetic peptide of claim 15 wherein said RV protein is the E2 protein and said amino acid sequence is contained within amino acids 1 to 257 (SEQ ID NO:76) of the E2 protein of RV strain M33 or the corresponding amino acids of other strains of RV.

17. The synthetic peptide of claim 15 wherein said RV protein is the E2 protein and said amino acid sequence is contained within amino acids 1 to 40 of the E2 protein.

18. The synthetic peptide of claim 17 wherein said amino acids 1 to 40 (SEQ ID NO: 77) of the E2 protein are those set forth in Table 2 for RV strain M33 or the corresponding amino acids of other strains of RV.

19. A synthetic peptide having an amino acid sequence of a portion of an E2 protein of rubella virus (RV) and which contains a human T-cell determinant wherein said amino acid sequence is contained within the sequence GLQPRADMAAPPNPPQPPRAPQPPRAHGQHYGHHHHQLPFLG (SEQ ID NO: 78).

* * * * *

UNITED STATES PATENT AND TRADEMARK OFFICE
CERTIFICATE OF CORRECTION

PATENT NO.    : 6,037,448
DATED         : March 14, 2000
INVENTOR(S)   : Pele Chong et al Page 1 of 1

It is certified that error appears in the above-identified patent and that said Letters Patent is hereby corrected as shown below:

Assignee: Connaught Laboratories Limited and University of British Columbia

Signed and Sealed this

Fifth Day of June, 2001

*Attest:*

*Attesting Officer*

NICHOLAS P. GODICI

*Acting Director of the United States Patent and Trademark Office*

SEQUENCE LISTING (1) GENERAL INFORMATION:

(iii) NUMBER OF SEQUENCES: 78

(2) INFORMATION FOR SEQ ID NO:1:

(i) SEQUENCE CHARACTERISTICS:
       (A) LENGTH: 22 amino acids
       (B) TYPE: amino acid
       (C) STRANDEDNESS: single
       (D) TOPOLOGY: linear (xi) SEQUENCE DESCRIPTION: SEQ ID NO:1:

Glu Glu Ala Phe Thr Tyr Leu Cys Thr Ala Pro Gly Cys Ala Thr Gln
   1               5                   10                  15

Thr Pro Val Pro Val Arg
               20

(2) INFORMATION FOR SEQ ID NO:2:

(i) SEQUENCE CHARACTERISTICS:
       (A) LENGTH: 20 amino acids
       (B) TYPE: amino acid
       (C) STRANDEDNESS: single
       (D) TOPOLOGY: linear (xi) SEQUENCE DESCRIPTION: SEQ ID NO:2:

Val Pro Val Arg Leu Ala Gly Val Gly Phe Glu Ser Lys Ile Val Asp
   1               5                   10                  15

Gly Gly Cys Phe
               20

(2) INFORMATION FOR SEQ ID NO:3:

(i) SEQUENCE CHARACTERISTICS:
       (A) LENGTH: 20 amino acids
       (B) TYPE: amino acid
       (C) STRANDEDNESS: single
       (D) TOPOLOGY: linear (xi) SEQUENCE DESCRIPTION: SEQ ID NO:3:

Phe Ala Pro Trp Asp Leu Glu Ala Thr Gly Ala Cys Ile Cys Glu Ile
   1               5                   10                  15

Pro Thr Asp Val
               20

(2) INFORMATION FOR SEQ ID NO:4:

(i) SEQUENCE CHARACTERISTICS:
       (A) LENGTH: 21 amino acids
       (B) TYPE: amino acid
       (C) STRANDEDNESS: single
       (D) TOPOLOGY: linear (xi) SEQUENCE DESCRIPTION: SEQ ID NO:4:

Pro Thr Asp Val Ser Cys Glu Gly Leu Gly Ala Trp Val Pro Thr Ala
   1               5                   10                  15

Pro Cys Ala Arg Ile
               20

(2) INFORMATION FOR SEQ ID NO:5:

(i) SEQUENCE CHARACTERISTICS:

(A) LENGTH: 21 amino acids
        (B) TYPE: amino acid
        (C) STRANDEDNESS: single
        (D) TOPOLOGY: linear (xi) SEQUENCE DESCRIPTION: SEQ ID NO:5:

Cys Ala Arg Ile Trp Asn Gly Thr Gln Arg Ala Cys Thr Phe Trp Ala
    1               5                  10                  15

Val Asn Ala Tyr Ser
                20

(2) INFORMATION FOR SEQ ID NO:6:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:6:

Gly Ser Tyr Tyr Lys Gln Tyr His Pro Thr Ala Cys Glu Val Glu Pro
    1               5                  10                  15

Ala Phe Gly His
                20

(2) INFORMATION FOR SEQ ID NO:7:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:7:

Ala Phe Gly His Ser Asp Ala Ala Cys Trp Gly Phe Pro Thr Asp Thr
    1               5                  10                  15

Val Met Ser Val
                20

(2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:8:

Ser Val Phe Ala Leu Ala Ser Tyr Val Gln His Pro His Lys Thr Val
    1               5                  10                  15

Arg Val Lys Phe
                20

(2) INFORMATION FOR SEQ ID NO:9:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:9:

Val Lys Phe His Thr Glu Thr Arg Thr Val Trp Gln Leu Ser Val Ala
    1               5                  10                  15

Gly Val Ser Cys

20

(2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:10:

```
Val Ser Cys Asn Val Thr Thr Glu His Pro Phe Cys Asn Thr Pro His
1               5                   10                  15

Gly Gln Leu Glu
            20
```

(2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:11:

```
Gly Gln Leu Glu Val Gln Val Pro Pro Asp Pro Gly Asp Leu Val Glu
1               5                   10                  15

Tyr Ile Met Asn
            20
```

(2) INFORMATION FOR SEQ ID NO:12:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:12:

```
Ile Met Asn Tyr Thr Gly Asn Gln Gln Ser Arg Trp Gly Leu Gly Ser
1               5                   10                  15

Pro Asn Cys His
            20
```

(2) INFORMATION FOR SEQ ID NO:13:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:13:

```
Asn Cys His Gly Pro Asp Trp Ala Ser Pro Val Cys Gln Arg His Ser
1               5                   10                  15

Pro Asp Cys Ser
            20
```

(2) INFORMATION FOR SEQ ID NO:14:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:14:

Pro Asp Cys Ser Arg Leu Val Gly Ala Thr Pro Glu Arg Pro Arg Leu
1               5                   10                  15

Arg Leu Val Asp
            20

(2) INFORMATION FOR SEQ ID NO:15:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:15:

Arg Leu Val Asp Ala Asp Asp Pro Leu Leu Arg Thr Ala Pro Gly Pro
1               5                   10                  15

Gly Glu Val Trp
            20

(2) INFORMATION FOR SEQ ID NO:16:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:16:

Gly Glu Val Trp Val Thr Pro Val Ile Gly Ser Gln Ala Arg Lys Cys
1               5                   10                  15

Gly Leu His Ile
            20

(2) INFORMATION FOR SEQ ID NO:17:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:17:

Leu His Ile Arg Ala Gly Pro Tyr Gly His Ala Thr Val Glu Met Pro
1               5                   10                  15

Glu Trp Ile His
            20

(2) INFORMATION FOR SEQ ID NO:18:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:18:

Ile His Ala His Thr Thr Ser Asp Pro Trp His Pro Pro Gly Pro Leu
1               5                   10                  15

Gly Leu Lys Phe
            20

(2) INFORMATION FOR SEQ ID NO:19:

```
    (i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:19:

Leu Lys Phe Lys Thr Val Arg Pro Val Ala Leu Pro Arg Ala Leu Ala
    1               5                   10                  15

Pro Pro Arg Asn
                20

(2) INFORMATION FOR SEQ ID NO:20:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:20:

Pro Arg Asn Val Arg Val Thr Gly Cys Tyr Gln Cys Gly Thr Pro Ala
    1               5                   10                  15

Leu Val Glu Gly
                20

(2) INFORMATION FOR SEQ ID NO:21:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:21:

Val Glu Gly Leu Ala Pro Gly Gly Gly Asn Cys His Leu Thr Val Asn
    1               5                   10                  15

Gly Glu Asp Val
                20

(2) INFORMATION FOR SEQ ID NO:22:

(i) SEQUENCE CHARACTERISTICS:
        (A) LENGTH: 17 amino acids
        (B) TYPE: amino acid
        (C) STRANDEDNESS: single
        (D) TOPOLOGY: linear (xi) SEQUENCE DESCRIPTION: SEQ ID NO:22:

Gly Glu Asp Val Gly Ala Phe Pro Pro Gly Lys Phe Val Thr Ala Ala
    1               5                   10                  15

Leu (2) INFORMATION FOR SEQ ID NO:23:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO:23:

Leu Asn Thr Pro Pro Tyr Gln Val Ser Cys Gly Gly Glu Ser Asp
    1               5                   10                  15

Arg Ala Ser Ala Gly His
```

20

(2) INFORMATION FOR SEQ ID NO:24:

(i) SEQUENCE CHARACTERISTICS:
        (A) LENGTH: 17 amino acids
        (B) TYPE: amino acid
        (C) STRANDEDNESS: single
        (D) TOPOLOGY: linear (xi) SEQUENCE DESCRIPTION: SEQ ID NO:24:

Val Pro Pro Asp Pro Gly Asp Leu Val Glu Tyr Ile Met Asn Tyr Thr
    1               5                   10                  15

Gly (2) INFORMATION FOR SEQ ID NO:25:

(i) SEQUENCE CHARACTERISTICS:
        (A) LENGTH: 36 amino acids
        (B) TYPE: amino acid
        (C) STRANDEDNESS: single
        (D) TOPOLOGY: linear (xi) SEQUENCE DESCRIPTION: SEQ ID NO:25:

Pro Asp Pro Gly Asp Leu Val Glu Tyr Ile Met Asn Tyr Thr Gly Asn
    1               5                   10                  15

Gln Gln Ser Arg Trp Gly Leu Gly Ser Pro Asn Cys His Gly Pro Asp
                20                  25                  30

Trp Ala Ser Pro
                35

(2) INFORMATION FOR SEQ ID NO:26:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:26:

Gly Leu Gly Ser Pro Asn Cys His Gly Pro Asp Trp Ala Ser Pro
    1               5                   10                  15

(2) INFORMATION FOR SEQ ID NO:27:

(i) SEQUENCE CHARACTERISTICS:
        (A) LENGTH: 43 amino acids
        (B) TYPE: amino acid
        (C) STRANDEDNESS: single
        (D) TOPOLOGY: linear (xi) SEQUENCE DESCRIPTION: SEQ ID NO:27:

Pro Asp Pro Gly Asp Leu Val Glu Tyr Ile Met Asn Tyr Thr Gly Asn
    1               5                   10                  15

Gln Gln Ser Arg Trp Gly Leu Gly Ser Pro Asn Cys His Gly Pro Asp
                20                  25                  30

Trp Ala Ser Pro Val Cys Gln Arg His Ser Pro
                35                  40

(2) INFORMATION FOR SEQ ID NO:28:

(i) SEQUENCE CHARACTERISTICS:
        (A) LENGTH: 29 amino acids
        (B) TYPE: amino acid
        (C) STRANDEDNESS: single -continued (D) TOPOLOGY: linear (xi) SEQUENCE DESCRIPTION: SEQ ID NO:28:

Gly Asn Gln Gln Ser Arg Trp Gly Leu Gly Ser Pro Asn Cys His Gly
    1               5                  10                  15

Pro Asp Trp Ala Ser Pro Val Cys Gln Arg His Ser Pro
                20                  25

(2) INFORMATION FOR SEQ ID NO:29:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:29:

Gly Leu Gln Pro Arg Ala Asp Met Ala Ala Pro Pro Asn Pro Pro Gln
    1               5                  10                  15

Pro Pro Arg Ala
                20

(2) INFORMATION FOR SEQ ID NO:30:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO:30:

Pro Gln Pro Pro Arg Ala His Gly Gln His Tyr Gly His His His His
    1               5                  10                  15

Gln Leu Pro Phe Leu Gly
                20

(2) INFORMATION FOR SEQ ID NO:31:

(i) SEQUENCE CHARACTERISTICS:
        (A) LENGTH: 25 amino acids
        (B) TYPE: amino acid
        (C) STRANDEDNESS: single
        (D) TOPOLOGY: linear (xi) SEQUENCE DESCRIPTION: SEQ ID NO:31:

Pro Phe Leu Gly His Asp Gly His His Gly Thr Leu Arg Val Gly
    1               5                  10                  15

Gln His His Arg Asn Ala Ser Asp Val
                20                  25

(2) INFORMATION FOR SEQ ID NO:32:

(i) SEQUENCE CHARACTERISTICS:
        (A) LENGTH: 21 amino acids
        (B) TYPE: amino acid
        (C) STRANDEDNESS: single
        (D) TOPOLOGY: linear (xi) SEQUENCE DESCRIPTION: SEQ ID NO:32:

Ala Ser Asp Val Leu Pro Gly His Trp Leu Gln Gly Gly Trp Gly Cys
    1               5                  10                  15

Tyr Asn Leu Ser Asp
                20

(2) INFORMATION FOR SEQ ID NO:33:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:33:

```
Cys Tyr Asn Leu Ser Asp Trp His Gln Gly Thr His Val Cys His Thr
1               5                   10                  15

Lys His Met Asp Phe Trp Cys
            20
```

(2) INFORMATION FOR SEQ ID NO:34:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO:34:

```
Met Asp Phe Trp Cys Val Glu His Asp Arg Pro Pro Pro Pro Ala Thr
1               5                   10                  15

Pro Thr Ser Leu Thr Thr
            20
```

(2) INFORMATION FOR SEQ ID NO:35:

(i) SEQUENCE CHARACTERISTICS:
        (A) LENGTH: 21 amino acids
        (B) TYPE: amino acid
        (C) STRANDEDNESS: single
        (D) TOPOLOGY: linear (xi) SEQUENCE DESCRIPTION: SEQ ID NO:35:

```
Ser Leu Thr Thr Ala Ala Asn Tyr Ile Ala Ala Ala Thr Pro Ala Thr
1               5                   10                  15

Ala Pro Pro Pro Cys
            20
```

(2) INFORMATION FOR SEQ ID NO:36:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:36:

```
Cys His Ala Ala Gly Leu Asn Asp Ser Cys Gly Gly Phe Leu Ser Gly
1               5                   10                  15

Cys Gly Pro Met Arg Leu Pro
            20
```

(2) INFORMATION FOR SEQ ID NO:37:

(i) SEQUENCE CHARACTERISTICS:
        (A) LENGTH: 21 amino acids
        (B) TYPE: amino acid
        (C) STRANDEDNESS: single
        (D) TOPOLOGY: linear (xi) SEQUENCE DESCRIPTION: SEQ ID NO:37:

```
Cys Gly Pro Met Arg Leu Pro Thr Ala Leu Thr Pro Gly Ala Val Gly
```

```
            1               5              10              15

Asp Leu Arg Ala Val
                        20

(2) INFORMATION FOR SEQ ID NO:38:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO:38:

Leu Arg Ala Val His His Arg Pro Val Pro Ala Tyr Pro Val Cys Cys
        1               5                  10                  15

Ala Met Arg Trp Gly Leu
                        20

(2) INFORMATION FOR SEQ ID NO:39:

(i) SEQUENCE CHARACTERISTICS:
        (A) LENGTH: 24 amino acids
        (B) TYPE: amino acid
        (C) STRANDEDNESS: single
        (D) TOPOLOGY: linear (xi) SEQUENCE DESCRIPTION: SEQ ID NO:39:

Gly Leu Pro Pro Trp Glu Leu Val Ile Leu Thr Ala Arg Pro Glu Asp
        1               5                  10                  15

Gly Trp Thr Cys Arg Gly Val Pro
                        20

(2) INFORMATION FOR SEQ ID NO:40:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO:40:

Cys Arg Gly Val Pro Ala His Pro Gly Thr Arg Cys Pro Glu Leu Val
        1               5                  10                  15

Ser Pro Met Gly Arg Ala Thr Cys Ser Pro
                        20              25

(2) INFORMATION FOR SEQ ID NO:41:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO:41:

Cys Ser Pro Ala Ser Ala Leu Trp Leu Ala Thr Ala Asn Ala Leu Ser
        1               5                  10                  15

Leu Asp His Ala Phe Ala
                        20

(2) INFORMATION FOR SEQ ID NO:42:

(i) SEQUENCE CHARACTERISTICS:
        (A) LENGTH: 25 amino acids
        (B) TYPE: amino acid
```

(C) STRANDEDNESS: single
(D) TOPOLOGY: linear (xi) SEQUENCE DESCRIPTION: SEQ ID NO:42:

Ser Leu Asp His Ala Phe Ala Ala Phe Val Leu Leu Val Pro Trp Val
1               5                   10                  15

Leu Ile Phe Met Val Cys Arg Arg Ala
            20                  25

(2) INFORMATION FOR SEQ ID NO:43:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO:43:

Cys Arg Arg Ala Cys Arg Arg Pro Ala Pro Pro Pro Ser Pro Gln
1               5                   10                  15

Ser Ser Cys Arg Gly Thr Thr Pro Pro Ala Tyr Gly
            20                  25

(2) INFORMATION FOR SEQ ID NO:44:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:44:

Met Ala Ser Thr Thr Pro Ile Thr Met Glu Asp Leu Gln Lys Ala Leu
1               5                   10                  15

Glu Ala Gln Ser Arg Ala Leu Arg Ala Gly Leu Ala Ala Gly
            20                  25                  30

(2) INFORMATION FOR SEQ ID NO:45:

(i) SEQUENCE CHARACTERISTICS:
        (A) LENGTH: 29 amino acids
        (B) TYPE: amino acid
        (C) STRANDEDNESS: single
        (D) TOPOLOGY: linear (xi) SEQUENCE DESCRIPTION: SEQ ID NO:45:

Ala Ala Gly Ala Ser Gln Ser Arg Arg Pro Arg Pro Arg His Ala
1               5                   10                  15

Arg Ala Gln His Leu Pro Glu Met Thr Pro Ala Val Thr
            20                  25

(2) INFORMATION FOR SEQ ID NO:46:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO:46:

Thr Pro Ala Val Thr Pro Glu Gly Pro Ala Pro Pro Arg Thr Gly Ala
1               5                   10                  15

Trp Gln Arg Lys Asp Trp Ser Arg Ala Pro Pro
            20                  25

(2) INFORMATION FOR SEQ ID NO:47:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO:47:

```
Ser Arg Ala Pro Pro Pro Glu Glu Arg Gln Glu Ser Arg Ser Gln
1               5                   10                  15

Thr Pro Ala Pro Lys Pro Ser Arg Ala Pro Pro
            20                  25
```

(2) INFORMATION FOR SEQ ID NO:48:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO:48:

```
Ser Arg Ala Pro Pro Gln Gln Pro Gln Pro Pro Arg Met Gln Thr Gly
1               5                   10                  15

Arg Gly Gly Ser Ala Pro Arg Pro Glu Leu Gly Pro
            20                  25
```

(2) INFORMATION FOR SEQ ID NO:49:

(i) SEQUENCE CHARACTERISTICS:
        (A) LENGTH: 34 amino acids
        (B) TYPE: amino acid
        (C) STRANDEDNESS: single
        (D) TOPOLOGY: linear (xi) SEQUENCE DESCRIPTION: SEQ ID NO:49:

```
Pro Glu Leu Gly Pro Pro Thr Asn Pro Phe Gln Ala Ala Val Ala Arg
1               5                   10                  15

Gly Leu Arg Pro Pro Leu His Asp Pro Asp Thr Glu Ala Pro Thr Glu
            20                  25                  30

Ala Cys
```

(2) INFORMATION FOR SEQ ID NO:50:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO:50:

```
Cys Val Thr Ser Trp Leu Trp Ser Glu Gly Glu Gly Ala Val Phe Tyr
1               5                   10                  15

Arg Val Asp Leu His Phe Ile Asn Leu Gly Thr Pro
            20                  25
```

(2) INFORMATION FOR SEQ ID NO:51:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO:51:

Gly Thr Pro Pro Leu Asp Glu Asp Gly Arg Trp Asp Pro Ala Leu Met
1               5                   10                  15

Tyr Asn Pro Cys Gly Pro Glu Pro Ala His Val
            20                  25

(2) INFORMATION FOR SEQ ID NO:52:

(i) SEQUENCE CHARACTERISTICS:
        (A) LENGTH: 29 amino acids
        (B) TYPE: amino acid
        (C) STRANDEDNESS: single
        (D) TOPOLOGY: linear (xi) SEQUENCE DESCRIPTION: SEQ ID NO:52:

Val Arg Ala Tyr Asn Gln Pro Ala Gly Asp Val Arg Gly Val Trp Gly
1               5                   10                  15

Lys Gly Glu Arg Thr Tyr Ala Glu Gln Asp Phe Arg Val
            20                  25

(2) INFORMATION FOR SEQ ID NO:53:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO:53:

Phe Arg Val Gly Gly Thr Arg Trp His Arg Leu Leu Arg Met Pro Val
1               5                   10                  15

Arg Gly Leu Asp Gly Asp Thr Ala Pro Leu Pro
            20                  25

(2) INFORMATION FOR SEQ ID NO:54:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO:54:

Pro Leu Pro Pro His Thr Thr Glu Arg Ile Glu Thr Arg Ser Ala Arg
1               5                   10                  15

His Pro Trp Arg Ile Arg Phe Gly Ala Pro
            20                  25

(2) INFORMATION FOR SEQ ID NO:55:

(i) SEQUENCE CHARACTERISTICS:
        (A) LENGTH: 32 amino acids
        (B) TYPE: amino acid
        (C) STRANDEDNESS: single
        (D) TOPOLOGY: linear (xi) SEQUENCE DESCRIPTION: SEQ ID NO:55:

Cys Ser Ser Val Arg Ala Tyr Asn Gln Pro Ala Gly Asp Val Arg Gly
1               5                   10                  15

Val Trp Gly Lys Gly Glu Arg Thr Tyr Ala Glu Gln Asp Phe Arg Val
            20                  25                  30

(2) INFORMATION FOR SEQ ID NO:56:

(i) SEQUENCE CHARACTERISTICS:
    (A) LENGTH: 75 amino acids
    (B) TYPE: amino acid
    (C) STRANDEDNESS: single
    (D) TOPOLOGY: linear (xi) SEQUENCE DESCRIPTION: SEQ ID NO:56:

Cys Ser Ser Val Arg Ala Tyr Asn Gln Pro Ala Gly Asp Val Arg Gly
1               5                   10                  15

Val Trp Gly Lys Gly Glu Arg Thr Tyr Ala Glu Gln Asp Phe Arg Val
            20                  25                  30

Pro Asp Pro Gly Asp Leu Val Glu Tyr Ile Met Asn Tyr Thr Gly Asn
        35                  40                  45

Gln Gln Ser Arg Trp Gly Leu Gly Ser Pro Asn Cys His Gly Pro Asp
    50                  55                  60

Trp Ala Ser Pro Val Cys Gln Arg His Ser Pro
65                  70                  75

(2) INFORMATION FOR SEQ ID NO:57:

(i) SEQUENCE CHARACTERISTICS:
        (A) LENGTH: 25 amino acids
        (B) TYPE: amino acid
        (C) STRANDEDNESS: single
        (D) TOPOLOGY: linear (xi) SEQUENCE DESCRIPTION: SEQ ID NO:57:

Cys Ser Ser Glu Glu Ala Phe Thr Tyr Leu Cys Thr Ala Pro Gly Cys
1               5                   10                  15

Ala Thr Gln Thr Pro Val Pro Val Arg
            20                  25

(2) INFORMATION FOR SEQ ID NO:58:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:58:

Cys Ser Ser Gly Ser Tyr Tyr Lys Gln Tyr His Pro Thr Ala Cys Glu
1               5                   10                  15

Val Glu Pro Ala Phe Gly His
            20

(2) INFORMATION FOR SEQ ID NO:59:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:59:

Cys Ser Ser Ser Val Phe Ala Leu Ala Ser Tyr Val Gln His Pro His
1               5                   10                  15

Lys Thr Val Arg Val Lys Phe
            20

(2) INFORMATION FOR SEQ ID NO:60:

(i) SEQUENCE CHARACTERISTICS:
        (A) LENGTH: 23 amino acids

```
       (B) TYPE: amino acid
       (C) STRANDEDNESS: single
       (D) TOPOLOGY: linear (xi) SEQUENCE DESCRIPTION: SEQ ID NO:60:

Cys Ser Ser Ile Met Asn Tyr Thr Gly Asn Gln Gln Ser Arg Trp Gly
  1               5                  10                  15

Leu Gly Ser Pro Asn Cys His
                  20

(2) INFORMATION FOR SEQ ID NO:61:

(i) SEQUENCE CHARACTERISTICS:
       (A) LENGTH: 23 amino acids
       (B) TYPE: amino acid
       (C) STRANDEDNESS: single
       (D) TOPOLOGY: linear (xi) SEQUENCE DESCRIPTION: SEQ ID NO:61:

Cys Ser Ser Leu His Ile Arg Ala Gly Pro Tyr Gly His Ala Thr Val
  1               5                  10                  15

Glu Met Pro Glu Trp Ile His
                  20

(2) INFORMATION FOR SEQ ID NO:62:

(i) SEQUENCE CHARACTERISTICS:
       (A) LENGTH: 23 amino acids
       (B) TYPE: amino acid
       (C) STRANDEDNESS: single
       (D) TOPOLOGY: linear (xi) SEQUENCE DESCRIPTION: SEQ ID NO:62:

Cys Ser Ser Leu Lys Phe Lys Thr Val Arg Pro Val Ala Leu Pro Arg
  1               5                  10                  15

Ala Leu Ala Pro Pro Arg Asn
                  20

(2) INFORMATION FOR SEQ ID NO:63:

(i) SEQUENCE CHARACTERISTICS:
       (A) LENGTH: 23 amino acids
       (B) TYPE: amino acid
       (C) STRANDEDNESS: single
       (D) TOPOLOGY: linear (xi) SEQUENCE DESCRIPTION: SEQ ID NO:63:

Cys Ser Ser Val Glu Gly Leu Ala Pro Gly Gly Asn Cys His Leu
  1               5                  10                  15

Thr Val Asn Gly Glu Asp Val
                  20

(2) INFORMATION FOR SEQ ID NO:64:

(i) SEQUENCE CHARACTERISTICS:
       (A) LENGTH: 39 amino acids
       (B) TYPE: amino acid
       (C) STRANDEDNESS: single
       (D) TOPOLOGY: linear (xi) SEQUENCE DESCRIPTION: SEQ ID NO:64:

Cys Ser Ser Pro Asp Pro Gly Asp Leu Val Glu Tyr Ile Met Asn Tyr
  1               5                  10                  15

Thr Gly Asn Gln Gln Ser Arg Trp Gly Leu Gly Ser Pro Asn Cys His
                  20                  25                  30
```

```
    Gly Pro Asp Trp Ala Ser Pro
            35
```

(2) INFORMATION FOR SEQ ID NO:65:

(i) SEQUENCE CHARACTERISTICS:
        (A) LENGTH: 45 amino acids
        (B) TYPE: amino acid
        (C) STRANDEDNESS: single
        (D) TOPOLOGY: linear (xi) SEQUENCE DESCRIPTION: SEQ ID NO:65:

```
    Cys Ser Ser Pro Asp Pro Gly Asp Leu Val Glu Tyr Ile Met Asn Tyr
    1               5                   10                  15

Thr Gly Asn Gln Gln Ser Arg Trp Gly Leu Gly Ser Pro Asn Cys His
                20                  25                  30

Gly Pro Asp Trp Ala Ser Pro Cys Gln Arg His Ser Pro
            35                  40                  45
```

(2) INFORMATION FOR SEQ ID NO:66:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO:66:

```
    Cys Ser Ser Pro Gln Pro Pro Arg Ala His Gly Gln His Tyr Gly His
    1               5                   10                  15

His His His Gln Leu Pro Phe Leu Gly Cys
                20                  25
```

(2) INFORMATION FOR SEQ ID NO:67:

(i) SEQUENCE CHARACTERISTICS:
        (A) LENGTH: 24 amino acids
        (B) TYPE: amino acid
        (C) STRANDEDNESS: single
        (D) TOPOLOGY: linear (xi) SEQUENCE DESCRIPTION: SEQ ID NO:67:

```
    Cys Ser Ser Ala Ser Asp Val Leu Pro Gly His Trp Leu Gln Gly Gly
    1               5                   10                  15

Trp Gly Cys Tyr Asn Leu Ser Asp
                20
```

(2) INFORMATION FOR SEQ ID NO:68:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO:68:

```
    Cys Ser Ser Cys Tyr Asn Leu Ser Asp Trp His Gln Gly Thr His Val
    1               5                   10                  15

Cys His Thr Lys His Met Asp Phe Trp Cys
                20                  25
```

(2) INFORMATION FOR SEQ ID NO:69:

(i) SEQUENCE CHARACTERISTICS:

(A) LENGTH: 24 amino acids
            (B) TYPE: amino acid
            (C) STRANDEDNESS: single
            (D) TOPOLOGY: linear (xi) SEQUENCE DESCRIPTION: SEQ ID NO:69:

Cys Ser Ser Ser Leu Thr Thr Ala Ala Asn Tyr Ile Ala Ala Ala Thr
    1               5                   10                  15

Pro Ala Thr Ala Pro Pro Pro Cys
                20

(2) INFORMATION FOR SEQ ID NO:70:

(i) SEQUENCE CHARACTERISTICS:
        (A) LENGTH: 25 amino acids
        (B) TYPE: amino acid
        (C) STRANDEDNESS: single
        (D) TOPOLOGY: linear (xi) SEQUENCE DESCRIPTION: SEQ ID NO:70:

Cys Ser Ser Leu Arg Ala Val His His Arg Pro Val Pro Ala Tyr Pro
    1               5                   10                  15

Val Cys Cys Ala Met Arg Trp Gly Leu
                20                  25

(2) INFORMATION FOR SEQ ID NO:71:

(i) SEQUENCE CHARACTERISTICS:
        (A) LENGTH: 37 amino acids
        (B) TYPE: amino acid
        (C) STRANDEDNESS: single
        (D) TOPOLOGY: linear (xi) SEQUENCE DESCRIPTION: SEQ ID NO:71:

Cys Ser Ser Pro Glu Leu Gly Pro Pro Thr Asn Pro Phe Gln Ala Ala
    1               5                   10                  15

Val Ala Arg Gly Leu Arg Pro Pro Leu His Asp Pro Asp Thr Glu Ala
                20                  25                  30

Pro Thr Glu Ala Cys
                35

(2) INFORMATION FOR SEQ ID NO:72:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO:72:

Cys Ser Ser Cys Val Thr Ser Trp Leu Trp Ser Glu Gly Glu Gly Ala
    1               5                   10                  15

Val Phe Tyr Arg Val Asp Leu His Phe Ile Asn Leu Gly Thr Pro
                20                  25                  30

(2) INFORMATION FOR SEQ ID NO:73:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO:73:

Cys Ser Ser Gly Thr Pro Pro Leu Asp Glu Asp Gly Arg Trp Asp Pro

```
            1               5                  10                 15
        Ala Leu Met Tyr Asn Pro Cys Gly Pro Glu Pro Pro Ala His Val
                        20              25                 30
```

(2) INFORMATION FOR SEQ ID NO:74:

(i) SEQUENCE CHARACTERISTICS:
        (A) LENGTH: 33 amino acids
        (B) TYPE: amino acid
        (C) STRANDEDNESS: single
        (D) TOPOLOGY: linear (xi) SEQUENCE DESCRIPTION: SEQ ID NO:74:

```
    Cys Ser Ser Cys Val Arg Ala Tyr Asn Gln Pro Ala Gly Asp Val Arg
    1               5                  10                 15

Gly Val Trp Gly Lys Gly Glu Arg Thr Tyr Ala Glu Gln Asp Phe Arg
                    20                 25                 30

Val
```

(2) INFORMATION FOR SEQ ID NO:75:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:75:

```
    Cys Ser Ser Pro Leu Pro Pro His Thr Thr Glu Arg Ile Glu Thr Arg
    1               5                  10                 15

Ser Ala Arg His Pro Trp Arg Ile Arg Phe Gly Ala Pro Cys
                    20                 25                 30
```

(2) INFORMATION FOR SEQ ID NO:76:

(i) SEQUENCE CHARACTERISTICS:
        (A) LENGTH: 257 amino acids
        (B) TYPE: amino acid
        (C) STRANDEDNESS: single
        (D) TOPOLOGY: linear (xi) SEQUENCE DESCRIPTION: SEQ ID NO:76:

```
    Gly Leu Gln Pro Arg Ala Asp Met Ala Ala Pro Pro Asn Pro Pro Gln
    1               5                  10                 15

Pro Pro Arg Ala His Gly Gln His Tyr Gly His His His Gln Leu
                    20                 25                 30

Pro Phe Leu Gly His Asp Gly His His Gly Gly Thr Leu Arg Val Gly
                35                 40                 45

Gln His His Arg Asn Ala Ser Asp Val Leu Pro Gly His Trp Leu Gln
                50                 55                 60

Gly Gly Trp Gly Cys Tyr Asn Leu Ser Asp Trp His Gln Gly Thr His
    65              70                 75                 80

Val Cys His Thr Lys His Met Asp Phe Trp Cys Val Glu His Asp Arg
                    85                 90                 95

Pro Pro Pro Pro Ala Thr Pro Thr Ser Leu Thr Thr Ala Ala Asn Tyr
                    100                105                110

Ile Ala Ala Ala Thr Pro Ala Thr Ala Pro Pro Cys His Ala Ala
                    115                120                125

Gly Leu Asn Asp Ser Cys Gly Gly Phe Leu Ser Gly Cys Gly Pro Met
                    130                135                140
```

```
Arg Leu Pro Thr Ala Leu Thr Pro Gly Ala Val Gly Asp Leu Arg Ala
145                 150                 155                 160

Val His His Arg Pro Val Pro Ala Tyr Pro Val Cys Cys Ala Met Arg
                165                 170                 175

Trp Gly Leu Pro Pro Trp Glu Leu Val Ile Leu Thr Ala Arg Pro Glu
                180                 185                 190

Asp Gly Trp Thr Cys Arg Gly Val Pro Pro Ala His Pro Gly Thr Arg
                195                 200                 205

Cys Pro Glu Leu Val Ser Pro Met Gly Arg Ala Thr Cys Ser Pro Ala
                210                 215                 220

Ser Ala Leu Trp Leu Ala Thr Ala Asn Ala Leu Ser Leu Asp His Ala
225                 230                 235                 240

Phe Ala Ala Phe Val Leu Leu Val Pro Trp Val Leu Ile Phe Met Val
                245                 250                 255

Cys
```

(2) INFORMATION FOR SEQ ID NO:77:

(i) SEQUENCE CHARACTERISTICS:
        (A) LENGTH: 40 amino acids
        (B) TYPE: amino acid
        (C) STRANDEDNESS: single
        (D) TOPOLOGY: linear (xi) SEQUENCE DESCRIPTION: SEQ ID NO:77:

```
Gly Leu Gln Pro Arg Ala Asp Met Ala Ala Pro Pro Asn Pro Pro Gln
1               5                   10                  15

Pro Pro Arg Ala His Gly Gln His Tyr Gly His His His Gln Leu
                20                  25                  30

Pro Phe Leu Gly His Asp Gly His
                35                  40
```

(2) INFORMATION FOR SEQ ID NO:78:

(i) SEQUENCE CHARACTERISTICS:
        (A) LENGTH: 42 amino acids
        (B) TYPE: amino acid
        (C) STRANDEDNESS: single
        (D) TOPOLOGY: linear (xi) SEQUENCE DESCRIPTION: SEQ ID NO:78:

```
Gly Leu Gln Pro Arg Ala Asp Met Ala Ala Pro Pro Asn Pro Pro Gln
1               5                   10                  15

Pro Pro Arg Ala Pro Gln Pro Pro Arg Ala His Gly Gln His Tyr Gly
                20                  25                  30

His His His His Gln Leu Pro Phe Leu Gly
                35                  40
```